US008013018B2

(12) United States Patent
Hayashibe et al.

(10) Patent No.: US 8,013,018 B2
(45) Date of Patent: Sep. 6, 2011

(54) AMINOINDANE DERIVATIVE OR SALT THEREOF

(75) Inventors: Satoshi Hayashibe, Tokyo (JP); Shingo Yamasaki, Tokyo (JP); Kazushi Watanabe, Tokyo (JP); Nobuyuki Shiraishi, Tokyo (JP); Daisuke Suzuki, Tokyo (JP); Hiroaki Hoshii, Tokyo (JP); Junya Ohmori, Tokyo (JP); Takatoshi Kanayama, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 411 days.

(21) Appl. No.: 12/305,254

(22) PCT Filed: Jul. 17, 2007

(86) PCT No.: PCT/JP2007/064072
§ 371 (c)(1),
(2), (4) Date: Dec. 17, 2008

(87) PCT Pub. No.: WO2008/010481
PCT Pub. Date: Jan. 24, 2008

(65) Prior Publication Data
US 2009/0186916 A1 Jul. 23, 2009

(30) Foreign Application Priority Data
Jul. 18, 2006 (JP) ................ P2006-195307

(51) Int. Cl.
*A01N 37/12* (2006.01)
*A01N 37/44* (2006.01)
*A01N 33/18* (2006.01)
*A01N 33/24* (2006.01)
*A61K 31/24* (2006.01)
*A61K 31/04* (2006.01)

(52) U.S. Cl. ...................... 514/579; 514/740

(58) Field of Classification Search .......... 514/579, 514/740
See application file for complete search history.

(56) References Cited

U.S. PATENT DOCUMENTS

| 5,061,703 | A | 10/1991 | Bormann et al. |
| 5,639,913 | A | 6/1997 | Lidor et al. |
| 6,034,134 | A | 3/2000 | Gold et al. |
| 6,071,966 | A | 6/2000 | Gold et al. |
| 2002/0068839 | A1 | 6/2002 | Cohen et al. |
| 2003/0181445 | A1 | 9/2003 | Moltzen et al. |
| 2004/0167171 | A1 | 8/2004 | Ohkawa et al. |
| 2007/0197594 | A1 | 8/2007 | Hayashibe et al. |

FOREIGN PATENT DOCUMENTS

| CA | 2 580 980 | 3/2006 |
| JP | 9-510188 | 10/1997 |
| JP | 2821233 | 8/1998 |
| JP | 2003-081959 | 3/2003 |
| JP | 2004-504393 | 2/2004 |
| WO | 95/18617 | 7/1995 |
| WO | 99/01416 | 1/1999 |
| WO | 2006/033318 | 3/2006 |

*Primary Examiner* — Yong Chong
(74) *Attorney, Agent, or Firm* — Fitzpatrick, Cella, Harper & Scinto

(57) ABSTRACT

Provided is a compound that is an NMDA receptor antagonist having a broader safety margin, and is useful as an agent for treating or preventing Alzheimer's disease, cerebrovascular dementia, Parkinson's disease, ischemic apoplexy, or pain.
A novel compound or a salt thereof, which is characterized in that it has an amino group and $R^1$ (lower alkyl, cycloalkyl, -lower alkylene-aryl, aryl which may be substituted, and the like) on carbon atoms of indane, cyclopenta[b]thiophene, cyclopenta[b]furan, cyclopenta[b]pyridine, or cyclopenta[c]pyridine ring, or 2,3-dihydro-1-benzofuran, 2,3-dihydro-1-benzothiophene, indoline ring, or the like, and has $R^2$ and $R^3$ (the same or different, each lower alkyl or aryl) on carbon atoms beside them, and an NMDA receptor antagonist comprising the same as an active component.

14 Claims, No Drawings

AMINOINDANE DERIVATIVE OR SALT THEREOF

TECHNICAL FIELD

The present invention relates to an aminoindane derivative or a salt thereof which is useful as a medicine, especially as an NMDA receptor antagonist, and to an NMDA receptor antagonist comprising the same as an active ingredient. The aminoindane derivative or a salt thereof and the NMDA receptor antagonist comprising the same as an active ingredient, of the present invention, are useful for treating or preventing Alzheimer's disease, cerebrovascular dementia, Parkinson's disease, ischemic apoplexy, pain, and the like.

BACKGROUND ART

Glutamic acid acts as a neurotransmitter in the central nervous system of mammals, and controls the activity of neurocytes or the release of neurotransmitters via a glutamate receptor existing in synapses. At present, a glutamate receptor is classified into an "ionotropic glutamate receptor" and a "metabotropic glutamate receptor" from many pharmacological and biological studies (Hollmann M. and Heinemann S., Annu. Rev. Neurosci., 17 (1994) 31-108). An NMDA (N-methyl-D-aspartate) receptor is an ion-channel glutamate receptor specifically sensitive to the agonist NMDA (Moriyoshi K. et al., Nature, 354 (1991) 31-37; Meguro H. et al., Nature, 357 (1992) 70-74); and this has high $Ca^{2+}$ permeability (Iino M. et al., J. Physiol., 424 (1990) 151-165). The NMDA receptor is expressed with a specific pattern in a central nervous system (Ozawa S. et al., Prog. Neurobiol., 54 (1998) 581-618).

From many pharmacological and biological studies, it is believed that an NMDA receptor may participate in high-order neurologic functions such as memory and learning (Morris R G., et al., Nature, 319 (1986) 774-776; Tsien J Z. et al., Cell, 87 (1996) 1327-1338). On the other hand, it is suggested that the acute or chronic NMDA receptor hyperactivity or hypoactivity may participate in various nervous system diseases, for example, ischemic apoplexy, hemorrhagic brain injury, traumatic brain injury, neurodegenerative disorders (e.g., Alzheimer's disease, cerebrovascular dementia, Parkinson's disease, Huntington's disease, amyotrophic lateral sclerosis), glaucoma, AIDS encephalopathy, dependence, schizophrenia, depression, mania, stress-related diseases, epilepsy, and pain (Beal M F., FASEB J., 6 (1992) 3338-3344; Heresco-Levy U. and Javitt D C., Euro. Neuropsychopharmacol., 8 (1998) 141-152; Hewitt D J., Clin. J. Pain, 16 (2000) S73-79). Accordingly, drugs capable of controlling the activity of an NMDA receptor would be extremely useful in clinical application.

As drugs capable of controlling the activity of an NMDA receptor, a large number of non-competitive NMDA receptor antagonists are reported, but many of them have not been used in clinical application because of their side effects based on the NMDA receptor-antagonizing effect thereof, for example, mental aberration such as hallucination or confusion, and giddiness. Some of already-existing NMDA receptor antagonists, for example, ketamine and dextromethorphan have been tried against pain in clinical application (Fisher K. et al., J. Pain Symptom Manage., 20 (2000) 358-373), but the safety margin in the treatment with them is narrow, and their clinical use is limitative (Eide P K., et al., Pain, 58 (1994) 347-354). Memantine is known as a non-competitive NMDA receptor antagonist that has comparatively few side effects (Parsons C G., et al., Neuropharmacol., 38 (1999) 735-767); and recently, it has been reported that this may be effective for Alzheimer's disease (Reisberg B., et al., N. Engl. J. Med., 348 (2003) 1333-1341). However, the safety margin of memantine as a medicine is still not satisfactory, and an NMDA receptor antagonist having a broader safety margin is desired (Ditzler K., Arzneimittelforschung, 41 (1991) 773-780; Maier C., et al., Pain, 103 (2003) 277-283; Riederer P., et al., Lancet, 338 (1991) 1022-1023). It is expected that creation of such an NMDA receptor antagonist having a broader safety margin may bring about new clinical usefulness of the NMDA receptor antagonist.

Patent Document 1 describes a pharmaceutical composition for preventing and treating cerebral ischemia, which comprises an adamantane derivative represented by the following general formula or its pharmaceutically acceptable acid-addition salt:

[Chem. 1]

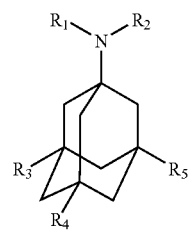

(wherein $R_1$ and $R_2$ are the same or different, and each represent hydrogen, a linear or branched alkyl group having 1 to 6 carbon atoms, or the like; $R_3$ and $R_4$ are the same or different, and each represent hydrogen, an alkyl group having 1 to 6 carbon atoms, or the like; and $R_5$ represents hydrogen or a linear or branched alkyl group having 1 to 6 carbon atoms. See the official gazette for other symbols in the formula).

In Patent Document 1, the above-mentioned memantine is described as Test Compound No. 1 (memantine is a compound of the formula wherein $R_1$, $R_2$ and $R_3$ are hydrogen atoms, and $R_4$ and $R_5$ are methyl).

Furthermore, Patent Document 2 describes 1-amino-alkylcyclohexane represented by the following general formula as an NMDA receptor antagonist.

[Chem. 2]

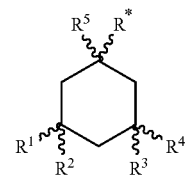

(wherein R* is —$(CH_2)_n$—$(CR^6R^7)_m$—$NR^8R^9$; n+m=0, 1 or 2; $R^1$ to $R^9$ are each independently selected from a group consisting of a hydrogen atom and $C_{1-6}$ lower alkyl; and at least $R^1$, $R^4$ and $R^5$ are lower alkyl. See the official gazette for other symbols in the formula).

Furthermore, the present Applicant reports a cyclic amine derivative represented by the following general formula, as an NMDA receptor antagonist in Patent Document 3.

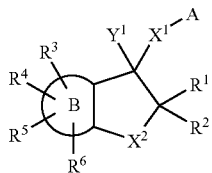

[Chem. 3]

(wherein A represents a 5- to 8-membered cyclic amine optionally having a double bond, optionally having a bridge structure and optionally having substituents of $R^7$ to $R^{11}$ in the ring, —$NH_2$, —NH(lower alkyl), or —N(lower alkyl)$_2$; ring B represents benzene, thiophene, furan, pyrrole, a 5- to 7-membered cycloalkane, or 5- to 7-membered cycloalkene; $X^1$ represents a bond, a lower alkylene, or -$L^3$-D-$L^4$-; and $Y^1$ represents —OH, —O-lower alkyl, —$NH_2$, or —$N_3$. See the official gazette for other symbols in the formula).

In addition, Patent Document 4 describes 1-aminoindane represented by the following general formula as a therapeutic agent for Parkinson's disease, and the like.

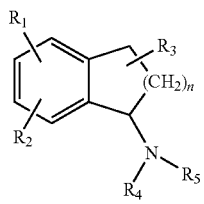

(wherein $R_1$ and $R_2$ independently represent hydrogen, hydroxy, alkyl, alkoxy, or the like; $R_3$ represents hydrogen, alkyl, hydroxy, alkoxy, and the like, $R_4$ and $R_5$ independently represent hydrogen, alkyl, aryl, or the like; and n represents 0, 1, or 2).

Patent Document 1: JP-A-2821233
Patent Document 2: Pamphlet of International Patent Publication WO 99/01416
Patent Document 3: Pamphlet of International Patent Publication WO 2006/033318
Patent Document 4: Pamphlet of International Patent Publication WO 95/18617

DISCLOSURE OF THE INVENTION

Problems to be Solved by the Invention

With the increase in the aging population, occurrence of Alzheimer's disease, cerebrovascular dementia, ischemic apoplexy and the like increases these days, and thus it is earnestly desired in the medical field to create an NMDA receptor antagonist having a broader safety margin, which is effective for treating or preventing such diseases as well as Parkinson's disease, pain, and the like. It is an object of the present invention to provide a novel aminoindane derivative or a salt thereof having an excellent NMDA receptor antagonistic activity and having a broader safety margin, and it is another object to provide a medicine comprising the same.

Means for Solving the Problems

The present inventors have found that a novel aminoindane derivative represented by the following general formula (I) or (Ia), or a salt thereof, which is characterized in that it has an amino group and $R^1$ (lower alkyl, cycloalkyl, -lower alkylene-aryl, aryl which may be substituted, and the like) on carbon atoms of indane, cyclopenta[b]thiophene, cyclopenta[b]furan, cyclopenta[b]pyridine, or cyclopenta[c]pyridine ring, or 2,3-dihydro-1-benzofuran, 2,3-dihydro-1-benzothiophene, indoline ring, or the like, and has $R^2$ and $R^3$ (the same or different, each lower alkyl or aryl) on carbon atoms beside them has an excellent NMDA receptor antagonistic activity and a broad safety margin, and thus have completed the present invention. Specifically, the present invention relates to an aminoindane derivative represented by the following general formula (I) or (Ia), or a salt thereof (hereinafter this may be referred to as "the compound (I) of the present invention" or "the compound (Ia) of the present invention"). Further, the present invention also relates to an NMDA receptor antagonist, especially a therapeutic agent or a preventing agent for Alzheimer's disease, cerebrovascular dementia, ischemic apoplexy, pain, etc., that comprises the compound (I) or (Ia), or a salt thereof of the present invention as an active component. Furthermore, the term "aminoindane derivative" as used in the present invention encompasses a wide range of "aminoindane analogs" having rings other than an indane ring, such as cyclopenta[b]thiophene, cyclopenta[b]furan, cyclopenta[b]pyridine, and cyclopenta[c]pyridine rings as described above, and it shall not be limited.

The compound (I) or (Ia) of the present invention is distinguished from the compounds as described in Patent Documents 3 and 4 in that it has an amino group, as well as $R^1$ (lower alkyl, cycloalkyl, -lower alkylene-aryl, aryl which may be substituted, and the like) other than a hydrogen atom on an indane ring, and the like, and has $R^2$ and $R^3$ (which may be the same or different, and each represent lower alkyl or aryl) other than hydrogen atoms on a positions thereof.

[1] A compound represented by the following general formula (I) or a salt thereof:

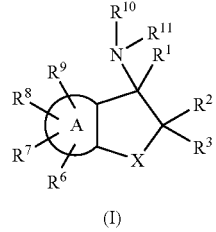

[Chem. 5]

(I)

(wherein the symbols in the formula (I) have the following meanings, respectively:

ring A: a 5- or 6-membered hetero ring, or a benzene ring,
X: $C(R^4)(R^5)$, O, S, or $N(R^{12})$,
$R^1$: lower alkyl, cycloalkyl, -lower alkylene-aryl, aryl which may be substituted, heteroaryl which may be substituted, or lower alkyl substituted with one or more halogens,
$R^2$ and $R^3$: the same or different, each lower alkyl, or aryl,
$R^4$ and $R^5$: the same or different, each a hydrogen atom, lower alkyl, —O-lower alkyl, —OH, -lower alkylene-OH, or -lower alkylene-O-lower alkyl,
$R^6$ to $R^9$: the same or different, each a hydrogen atom, lower alkyl, —O-lower alkyl, a halogen atom, lower alkyl substituted with one or more halogens, OH, CN, lower alkenyl, or a nitrogen-containing heterocyclic group,
$R^{10}$, and $R^{11}$: the same or different, each a hydrogen atom, or lower alkyl, and
$R^{12}$: a hydrogen atom or lower alkyl, provided that R² and R³ may be taken together with the adjacent carbon atom to form cycloalkyl).

[2] A compound represented by the following general formula (Ia) or a salt thereof:

[Chem. 6]

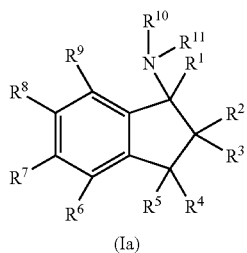

(Ia)

(wherein the symbols in the formula (Ia) above have the following meanings, respectively:
R¹: lower alkyl, cycloalkyl, -lower alkylene-aryl, aryl which may be substituted, heteroaryl which may be substituted, or lower alkyl substituted with one or more halogens,
R² and R³: the same or different, each lower alkyl, or aryl,
R⁴ and R⁵: the same or different, each a hydrogen atom, lower alkyl, —O-lower alkyl, —OH, -lower alkylene-OH, or -lower alkylene-O-lower alkyl,
R⁶ to R⁹: the same or different, each a hydrogen atom, lower alkyl, —O-lower alkyl, a halogen atom, lower alkyl substituted with one or more halogens, OH, CN, lower alkenyl, or a nitrogen-containing heterocyclic group,
R¹⁰ and R¹¹: the same or different, each a hydrogen atom, or lower alkyl,
provided that R² and R³ may be taken together with the adjacent carbon atom to form cycloalkyl).

[3] A compound or a salt thereof as described in [2], wherein R⁴, R⁵, R¹⁰, and R¹¹ in the formula (Ia) above are each a hydrogen atom.

[4] A compound or a salt thereof as described in [3], wherein R² and R³ in the formula (Ia) above are the same as or different from each other, and each are lower alkyl, or cycloalkyl formed in combination with the adjacent carbon atom.

[5] A compound or a salt thereof as described in [1], which is selected from 2,2-dimethyl-1-phenylindan-1-amine, 1-(4-fluorophenyl)-2,2-dimethylindan-1-amine, 1-(2-methoxyphenyl)-2,2-dimethylindan-1-amine, 1-(3-methoxyphenyl)-2,2-dimethylindan-1-amine, 1,2,2-trimethylindan-1-amine, 1,2,2,5-tetramethylindan-1-amine, 1,2,2,6-tetramethylindan-1-amine, 4-fluoro-1,2,2-trimethylindan-1-amine, 5-fluoro-1,2,2-trimethylindan-1-amine, 7-fluoro-1,2,2-trimethylindan-1-amine, 5-methoxy-1,2,2-trimethylindan-1-amine, 6-methoxy-1,2,2-trimethylindan-1-amine, 6-isopropoxy-1,2,2-trimethylindan-1-amine, 1-ethyl-2,2-dimethylindan-1-amine, 1-isopropyl-2,2-dimethylindan-1-amine, 1'-methyl-1',3'-dihydrospiro[cyclopropan-1,2'-inden]-1'-amine, 2,4,5,5-tetramethyl-5,5-dihydro-4H-cyclopenta[b]thiophen-4-amine.

[6] A pharmaceutical composition comprising a compound or a salt thereof as described in [1] or [2].

[7] A pharmaceutical composition as described in [6], which is an NMDA receptor antagonist.

[8] A pharmaceutical composition as described in [6], which is a therapeutic agent for dementia.

[9] A use of a compound or a salt thereof as described in [1] or [2] for preparation of an NMDA receptor antagonist or a therapeutic agent for dementia.

[10] A method for treating dementia, comprising administering a therapeutically effective amount of a compound or a salt thereof as described in [1] or [2] to a patient.

Effects of the Invention

The compound of the present invention have an NMDA receptor antagonistic activity, and is thus useful for treating or preventing Alzheimer's disease, cerebrovascular dementia, Parkinson's disease, ischemic apoplexy, pain, and the like.

BEST MODE FOR CARRYING OUT THE INVENTION

Hereinbelow, the present invention is described in detail.
Unless otherwise specifically indicated, the term "lower" as used in the definition of the general formulae in the present specification means a linear or branched carbon chain having 1 to 6 carbon atoms. Accordingly, "lower alkyl" is preferably linear or branched $C_{1-6}$ alkyl, and examples thereof include methyl, ethyl, propyl, isopropyl, butyl, isobutyl, sec-butyl, tert-butyl, pentyl, isopentyl, hexyl, and isohexyl. Among these, preferred are alkyls having 1 to 4 carbon atoms; and particularly preferred are methyl and ethyl.

Examples of the "lower alkylene" include methylene, ethylene, propylene, butylene, and also other branched lower alkylene. Preferred are lower alkylene having 1 to 3 carbon atoms; more preferred are methylene and ethylene; and particularly preferred is methylene.

Examples of the "halogen atom" include a fluorine atom, a chlorine atom, a bromine atom, and an iodine atom. Among these, preferred are a fluorine atom, a chlorine atom, and a bromine atom.

The "lower alkyl substituted with one or more halogens" means any of the hydrogen atoms of the "lower alkyl" as described above that is substituted with one or more "halogen atoms". Particularly preferred is $CF_3$.

The "cycloalkyl" means cycloalkyl having 3 to 8 carbon atoms.

The "R² and R³ are taken together with the adjacent carbon atom to form cycloalkyl" specifically means that cyclopropyl, cyclobutyl, cyclopentyl, or cyclohexyl are formed as such. Preferred is cyclopropyl.

Examples of the "lower alkenyl" include vinyl, 1- or 2-propenyl, isopropenyl, 2-methyl-1-propenyl, 2-methyl-2-propenyl, 1-methyl-1-propenyl, and 1-methyl-2-propenyl. Preferred is vinyl.

Examples of the "lower alkynyl" preferably include ethynyl, 1-propynyl, 2-propynyl, 1-butynyl, 2-butynyl, 3-butynyl, and 1-methyl-2-propynyl.

The "aryl" means a mono- to tri-cyclic aromatic hydrocarbon ring group having 6 to 14 carbon atoms. Preferably, examples thereof include phenyl, naphthyl, anthryl, and phenanthryl, and particularly preferred is phenyl.

The "heteroaryl" means a 5- or 6-membered aromatic hetero ring group having 1 to 4 hetero atoms selected from a nitrogen atom, an oxygen atom, and a sulfur atom. Preferably, examples thereof include thienyl, furyl, pyrrolyl, thiazolyl, pyridyl, and pyrimidyl, and particularly preferred is thienyl.

As the "-lower alkylene-aryl", particularly preferred are benzyl and phenethyl.

Examples of the "substituent" of the "aryl which may be substituted" or the "heteroaryl which may be substituted" include lower alkyl, —O-lower alkyl, a halogen atom, OH, CN, $CF_3$, —$NH_2$, —NH(lower alkyl), and —N(lower alkyl)₂, but not limited thereto.

The "nitrogen-containing hetero ring group" means a 3 to 7-membered monocyclic nitrogen-containing hetero ring group comprising 1 to 3 nitrogen atoms. Preferred is a 4 to 6-membered monocyclic saturated hetero ring group, and more preferred are azetidyl, pyrrolidyl, and piperidyl.

The "5- or 6-membered hetero ring" means thiophene, furan, pyridine rings, and the like. Thus, in the present invention, it is taken together with an adjacent cyclopentane ring to form 5,6-dihydro-5H-cyclopenta[b]thiophene,5,6-dihydro-5H-cyclopenta[b]furan, 6,7-dihydro-5H-cyclopenta[b]pyridine, 6,7-dihydro-5H-cyclopenta[c]pyridine rings, and the like.

Furthermore, "X" means hetero atoms such as O and S, or $NR^{12}$, as well as $C(R^4)(R^5)$. Here, $C(R^4)(R^5)$ means that carbon atoms have substituents of $R^4$ and $R^5$.

Further, the compounds of the present invention include mixtures of various isomers such as tautomers and optical isomers, as well as individual isomers isolated from them.

The compounds of the present invention may form acid-addition salts. Depending on the type of the substituent therein, the compounds may form salts with bases. Specifically, the salts include acid-addition salts with mineral acids such as hydrochloric acid, hydrobromic acid, hydroiodic acid, sulfuric acid, nitric acid, and phosphoric acid; organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; or acidic amino acids such as aspartic acid and glutamic acid; as well as salts with an inorganic base such as sodium, potassium, magnesium, calcium, and aluminum; an organic base such as methylamine, ethylamine, and ethanolamine; or a basic amino acid such as lysine, ornithine; and ammonium salts.

Further, the compounds of the present invention include hydrates, pharmaceutically acceptable various solvates, and crystalline polymorphic substances.

In addition, naturally, the compounds of the present invention are not limited to those described in the Examples as described below, and include all the compounds of the above general formula (I) or (Ia), and their pharmaceutically acceptable salts.

In addition, the compounds of the present invention include prodrugs that are metabolized in living bodies to give the compounds of the above formula (I) or (Ia), or compounds to be converted to their salts. Examples of the groups to form prodrugs of the compounds of the present invention include the groups as described in Prog. Med., 5:2157-2161 (1985), and the groups as described in Pharmaceutical Research, Drug Design, Hirokawa Publishing Company (1990), Vol. 7, Molecular Planning, p. 163-198.

[Production Processes]

Taking advantage of the characteristics based on the basic structure or the kind of the substituent therein, the compounds of the present invention may be prepared according to various known production processes. Depending on the kind of the functional group, the functional group in the starting compounds or intermediates may be modified into a suitable protected group, or a group that may be readily converted into a functional group, which may be technically effective in preparing the compounds. After the process, the protective group may be optionally removed, and an intended compound may thus be obtained, if necessary. Examples of the functional group include a hydroxyl group and a carboxyl group. Examples of their protective groups include the protective groups described in Greene & Wuts' "Protective Groups in Organic Synthesis", 2nd Ed. Depending on the reaction condition, these may be used suitably.

Typical production processes for the compounds (I) of the present invention are described below, but it goes without saying that the compounds (Ia) of the present invention can also be prepared by the methods.

(Production Processes)

The compound (Ib) of the present invention can be prepared by the method represented by the scheme 1. That is, indanone (1), and a Grignard reagent or an organic lithium reagent (2) can be reacted in an inert solvent such as tetrahydrofuran (hereinafter referred to as "THF"), diethyl ether and dichloromethane, from under cooling to at room temperature, and if desired, under heat, to give an alcohol (3). Then, (3) can be further reacted with an azidizing agent such as sodium azide and trimethylsilyl azide, in a solvent such as chloroform, 1,2-dichloroethane, and toluene, in the presence of an acid such as trifluoroacetic acid, sulfuric acid, and methane sulfonic acid, from under cooling to at room temperature, and if desired, under heat, to give an azide (4). Further, (4) can be subjected to catalytic hydrogen reduction, under a hydrogen atmosphere from at normal pressure to under a pressurized condition, in an inert solvent such as ethanol, ethyl acetate, THF, and acetic acid, using a catalyst such as palladium-carbon, a Raney nickel, and platinum oxide, from at room temperature to under the heating condition, or subjected to hydride reduction in a solvent such as THF and diethyl ether, from under cooling to under heat, using a reducing agent such as lithium aluminum hydride, and (4) can be further reacted with a phosphine reagent such as triphenylphophine, and tributyl phosphine, in a solvent such as THF, methanol, toluene, water, or a mixed solvent thereof, from at room temperature to under heat, to prepare a compound (Ib) wherein in the compound (I) of the present invention, both of $R^{10}$ and $R^{11}$ are all hydrogen atoms. Furthermore, (Ib) can be reacted with aldehyde in the presence of palladium-carbon, a rhodium carbon catalyst, or the like, in a solvent such as ethanol and THF, under a hydrogen atmosphere, from at room temperature to under heat to prepare a compound (Ic) wherein in the compound (I) of the present invention, at least one of $R^{10}$ and $R^{11}$ is a lower alkyl group. In addition, the compound (I) of the present invention is represented by either the following general formula (Ib) or (Ic).

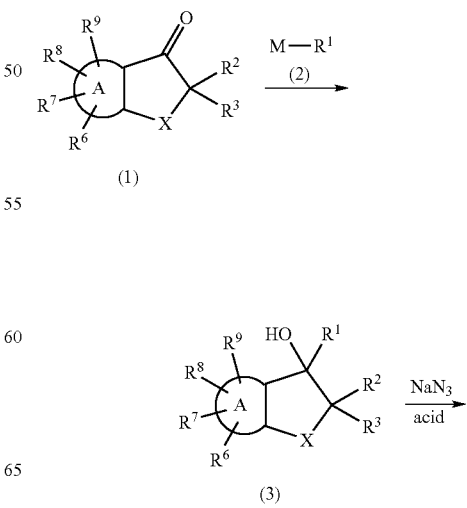

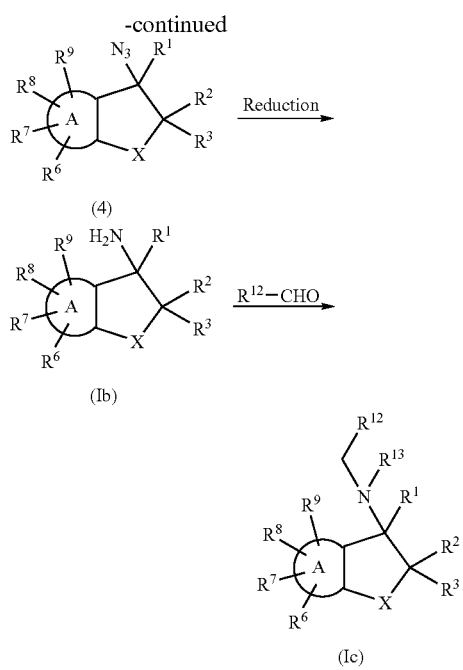

(wherein A, X, $R^1$ to $R^3$, and $R^6$ to $R^9$ each have the same meanings as described above. Further, $R^{12}$ represents hydrogen or a lower alkyl group, $R^{13}$ represents —$CH_2$—$R^{12}$ or a hydrogen atom, and M represents alkali metals such as lithium and magnesium halides)

The compounds (I) of the present invention may be subjected to reaction for group modification known to anyone skilled in the art to give a compound having a desired substituent. Typical reactions for it are described below.

Among the compounds (I) of the present invention, a compound wherein any one of $R^6$ to $R^9$ is a cyano group may be prepared by processing the corresponding compound where $R^6$ to $R^9$ are bromo groups with $Zn(CN)_2$ in the presence of a catalyst such as $Pd(PPh_3)_4$ in a solvent such as DMF and N-methylpiperidone under heat.

Among the compounds (1) of the present invention, in case where X is $C(R^4)(R^5)$, a compound wherein any one of $R^3$ to $R^6$ is an aryl group which may be substituted, lower alkenyl group, or a lower alkynyl group can be prepared by reacting the corresponding compound where any one of $R^3$ to $R^6$ is a bromo group or an iodo group, with an arylboronic acid, an alkenylboronic acid, an alkynylboronic acid, or a boronate ester thereof in the presence of a catalyst such as $Pd(PPh_3)_4$, $PdCl_2(dppf)$, or $Pd_2(dba)_3$ along with a base such as $K_2CO_3$, $Na_2CO_2$, KOH, CsF, and NaOEt, in a solvent such as DMF, N-methylpiperidone, DME, and toluene, or a mixed solvent thereof with water, under heat (Suzuki reaction).

Furthermore, the deprotection may be attained in a suitable solvent in the presence of a suitable base. Specific examples of the base include NaOH, KOH, NaOMe, and NaOEt. Specific examples of the solvent include ethers such as THF, dioxane, and diglyme; alcohols such as MeOH, EtOH, and i-PrOH; MeCN; water; or a mixed solvent. Depending on the type of the reaction substrate and the reaction condition, the solvent may be suitably selected. The reaction temperature may vary depending on the type of the starting compound and the reaction condition, generally covering from cooling to under reflux, preferably from about 0° C. to about 100° C.

In addition, the deprotection may also be attained in the presence of a metal catalyst such as Pd—C, $Pd(OH)_2$, and $PtO_2$ in a suitable solvent under a hydrogen atmosphere, but may be attained in the presence of a suitable Lewis acid in a suitable solvent. Examples of the Lewis acid are $BCl_3$, $BBr_3$, and $AlCl_3$, and examples of the solvent are ethers such as THF, dioxane; esters such as ethyl acetate; alcohols such as MeOH, EtOH; MeCN; and a mixture thereof. Depending on the type of the reaction substrate and the reaction condition, the solvent may be suitably selected. The reaction temperature may vary depending on the type of the starting compound and the reaction condition, generally covering from cooling to under reflux, preferably from about −80° C. to about 30° C.

Thus prepared, the compounds (I) of the present invention may be isolated as free compounds or as their pharmaceutically acceptable salts. A salt of the compounds (I) of the present invention may be prepared by processing the compounds (I) of the present invention that are in the form of free bases for ordinary reactions for salt formation.

The compound (I) of the present invention or a pharmaceutically acceptable salt thereof may be isolated and purified as their hydrates, solvates, or crystalline polymorphic substances. The isolation and purification may be attained through ordinary chemical treatment of extraction, concentration, evaporation, crystallization, filtration, recrystallization, and various types of chromatography.

Various isomers may be isolated by selecting suitable starting compounds, or by separating them based on the difference between the isomers in the physical or chemical properties thereof. For example, optical isomers may be led into stereochemically pure isomers by selecting suitable starting compounds or by racemic resolution of racemic compounds (for example, leading them into diastereomer salts with ordinary optically active acid for optical resolution).

2,2-Dimethyl-1-phenylindan-1-amine, 1-(4-fluorophenyl)-2,2-dimethylindan-1-amine, 1-(2-methoxy phenyl)-2,2-dimethylindan-1-amine, 1-(3-methoxy phenyl)-2,2-dimethylindan-1-amine, 1,2,2-trimethylindan-1-amine, 1,2,2,5-tetramethylindan-1-amine, 1,2,2,6-tetramethylindan-1-amine, 4-fluoro-1,2,2-trimethylindan-1-amine, 5-fluoro-1,2,2-trimethylindan-1-amine, 7-fluoro-1,2,2-trimethylindan-1-amine, 5-methoxy-1,2,2-trimethylindan-1-amine, 6-methoxy-1,2,2-trimethylindan-1-amine, 6-isopropoxy-1,2,2-trimethylindan-1-amine, 1-ethyl-2,2-dimethylindan-1-amine, 1-isopropyl-2,2-dimethylindan-1-amine, 1'-methyl-1',3'-dihydrospiro[cyclopropan-1,2'-inden]-1'-amine, 2,4,5,5-tetramethyl-5,5-dihydro-4H-cyclopenta[b]thiophen-4-amine of the compound of the present invention or a salt thereof can be subjected to optical resolution to its (R)-isomers and (S)-isomers by the above-described method.

The NMDA receptor antagonistic activity of the compounds of the present invention was confirmed by the following test methods.

1. MK-801 Binding Test:
1) Preparation of Specimens of Rat Meninges:

The whole brain was taken out from 30 10-week SD rats (Nippon SLC), and the cerebellum was removed from them. A 0.32 M sucrose solution was added to the part containing the cerebrum, cut in a mixer, and homogenized with a Teflon™ (trademark) homogenizer. This was centrifuged at 2800 rpm and 4° C. for 15 minutes, and the resulting supernatant was again centrifuged at 15000 g and 4° C. for 20 minutes. The pellets were suspended in 50 mM Tris-HCL (pH 7.5) containing 0.08% Triton X-100, and kept statically on ice for 30 minutes, then centrifuged at 15000 g and 4° C. for 20 minutes. The pellets were suspended in 50 mM Tris-HCl (pH 7.5) added thereto, and centrifuged at 15000 g and 4° C. for 20 minutes. 50 mM Tris-HCl (pH 7.5) was again added to the pellets, and centrifuged in the same manner as before. The pellets were suspended in 20 ml of 50 mM Tris-HCl (pH 7.5) added thereto, and homogenized with the Teflon™ (trademark) homogenizer. The membrane specimen was divided into small tubes and stored in a deep freezer (−80° C.). Before use, this was washed twice with 5 mM Tris-HCl (pH 7.5) of five times that of the membrane specimen. Its concentration was controlled at 1 mg protein/ml with 5 mM Tris-HCl (pH 7.5) added to it, and this was used for assay.

2) [$^3$H] MK-801 Binding Assay:

50 μl of the rat membrane specimen (1 mg protein/ml) was added to a solution of a test compound dissolved in 1 μl of DMSO. Then, 50 μl of a ligand solution (600 nM glutamate, 600 nM glycine, 8 nM [$^3$H] MK-801 (Perkin-Elmer) was added to it and well stirred, and reacted at room temperature for 45 minutes. Using Uni Filter Plate GF/B 96 (Perkin-Elmer) previously coated with 0.2% polyethyleneimine, the membrane specimen was collected, and the filter was well washed with 5 mM Tris-HCl (pH 7.5). 30 μl of Microscinti 20 (Perkin-Elmer) was added to the filter, and the radioactivity trapped by the filter was determined by a microplate scintillation counter (TopCount™ by Beckman). Based on the MK-801 (final 1 μM) inhibition, 100%, of a control case of DMSO alone, the concentration of the compound for 50% inhibition, $IC_{50}$ was computed. The [$^3$H]MK-801 binding affinity for the rat membrane specimen was obtained to be Kd=1.6 nM through Scatchard analysis. The Ki value of the compound was computed according to the calculation equation: $Ki=IC_{50}/(1+\text{radioligand concentration (4 nM) in assay})/Kd \text{ value (1.6 nM)}$).

As a result, the compounds of the present invention exhibited good NMDA receptor affinity. The Ki values of the NMDA receptor affinity of some typical compounds of the present invention are shown in Table 1 below.

TABLE 1

| Compound of the present invention | Ki (μM) |
|---|---|
| Example 2 | 0.4 |
| Example 10 | 0.4 |
| Example 17 | 0.8 |
| Example 18 | 0.3 |
| Example 21 | 0.1 |
| Example 23 | 0.9 |
| Example 36 | 0.4 |
| Example 37 | 0.1 |
| Example 38 | 0.3 |
| Example 41 | 0.8 |
| Example 42 | 0.3 |
| Example 43 | 0.3 |
| Example 44 | 0.6 |
| Example 48 | 0.6 |
| Example 59 | 0.9 |
| Example 61 | 0.5 |

2. Intracellular Calcium Concentration Determination Test by FLIPR (Fluorometric Imaging Plate Reader):

1) Preparation of Rat First-Generation Neurocytes:

Anesthetized with ether, Wistar rats (Nippon SLC) of pregnancy 19 days were let die from loss of blood by breast incision. The abdomen was cut open, and the womb was taken out, and the fetus was taken out of it. The whole brain was taken out, then the hemicerebrum was isolated in Neurobasal medium (Glu, Asp-free) (Gibco), and the meninx was removed. The hemicerebrum was recovered by centrifugation, and suspended in a cell-dispersing solution (0.36 mg/ml papain, 150 U/ml DNase 1, 0.02% L-cysteine monohydrochloride monohydrate, 0.02% bovine serum albumin, 0.5% glucose, $Ca^{2+}$, $Mg^{2+}$-free PBS), and processed at 37° C. for 15 minutes. This was centrifuged at 400 g for 5 minutes, and the supernatant was removed by suction. This was suspended in a neurocyte culture medium (Sumitomo Bakelite), and the cell masses were removed by filtration. The number of the living cells was counted, and 100,000 cells/well were incubated on a 96-well plate (Biocoat PDL96W black/clear, by Nippon Becton Dickinson) (at 37° C. in 5% $CO_2$).

2) Intracellular Calcium Concentration Determination by FLIPR (Fluorometric Imaging Plate Reader):

The culture of rat first-generation neurocytes (DIV7-9) was removed by suction, and the cells were washed once with a 100 μl assay buffer (Hank's Balanced Salt Solution ($Ca^{2+}$, $Mg^{2+}$-free), 20 mM Hepes-NaOH (pH 7.4), 1 mM $CaCl_2$). 100 μl of the assay buffer containing Fluo3 (Dojin Chemical) was added thereto, and incubated for 1 hour (37° C., 5% $CO_2$). The cells were washed three times with 100 μl of the assay buffer, and then a compound solution dissolved in 1 μl of DMSO, and 100 μl of the assay buffer containing 2.5 μM (final concentration) tetrodotoxin were added to it and incubated for 30 minutes (37° C., 5% $CO_2$). The fluorescent intensity was measured at intervals of 2 seconds. Ten seconds after the measurement start, 50 μl of a ligand solution (Hank's Balanced Salt Solution ($Ca^{2+}$,$Mg^{2+}$-free), 20 mM Hepes-NaOH (pH 7.4), 1 mM $CaCl_2$, 9 μM NMDA, 30 μM glycine) containing the test compound solution dissolved in 0.5 μl of DMSO was added to it, and the fluorescent intensity of the system was measured for 120 seconds from the start of the measurement. The data measured for 120 seconds (60 times in total) were averaged. Based on the 10 μM MK-801 inhibition with a control case of DMSO alone of 100%, the concentration of the compound for 50% inhibition, $IC_{50}$, was computed.

As a result, the compounds of the present invention exhibited a good NMDA receptor antagonizing effect.

The pharmaceutical composition that contains, as an active component thereof, one or more of the compounds of the present invention and their pharmaceutically acceptable salts may be formulated, in conjunction with carriers and vehicles for ordinary pharmaceutical application and other additives, as tablets, powders, infinitesimal grains, granules, capsules, pills, liquids, injections, suppositories, ointments, and fomentations, and is administered orally or parenterally.

The clinical dose to human of the compound of the present invention may be suitably determined, depending on the symptom, the body weight, the age and the sex of a patient to whom the compound is applied. It may be usually from 0.1 to 500 mg/adult/day for oral administration, and from 0.01 to 100 mg/adult/day for non-oral administration, and this may be administered all at once or in several times. The dose may vary under various conditions, and as the case may be, it may be smaller than the above-mentioned dose range.

The solid composition for oral administration of the compound of the present invention may be tablets, powders, granules, or the like. In the solid composition, one or more active substances may be mixed with at least one inert diluent, such as lactose, mannitol, glucose, hydroxypropyl cellulose, microcrystalline cellulose, starch, polyvinylpyrrolidone, and magnesium metasilicate aluminate. According to an ordinary manner, the composition may contain any other additive than such an inert diluent, for example, a lubricant such as magnesium stearate, a disintegrator such as calcium cellulose glycolate, a stabilizer such as lactose, a solubilizer, and a solubilizing adjuvant such as glutamic acid and aspartic acid. The tablets and pills may be coated with a sugar or with a gastric-coating or enteric-coating film.

The liquid composition for oral administration includes pharmaceutically acceptable emulsions, solutions, suspensions, syrups, and elixirs, and contains ordinary inert diluents such as purified water and ethyl alcohol. The composition may contain any other additives than such an inert diluent, for example, auxiliary agents such as a solubilizer, a dissolution promoter, a wetting agent, a suspending agent, as well as a sweetener, a flavoring, a fragrance, and a preservative. The injection for non-oral administration includes sterilized aqueous or non-aqueous solutions, suspensions, and emulsions. The diluent for the aqueous solution and suspension include, for example, distilled water for injection and physiological saline. The diluent for the non-aqueous solution and suspension includes, for example, propylene glycol, polyethylene glycol, vegetable oil such as olive oil, alcohols such as ethyl alcohols, Polysorbate 80 (traDe name).

The composition may further contain any other additive such as an isotonizer, a preservative, a wetting agent, an emulsifier, a dispersant, a stabilizer, a solubilizer, and a dissolution promoter. These may be sterilized by filtration through a bacteria-trapping filter, or by addition of a germicide, or through irradiation with light. As the case may be, a germ-free solid composition may be prepared, and it may be dissolved in germ-free water or germ-free solvent for injection to give the intended liquid composition before use.

EXAMPLES

Hereinbelow, the compounds of the present invention are described with reference to the following Examples. The starting compounds for the compounds of the present invention include novel compounds, and thus their production examples are illustrated as Reference Examples.

Reference Example 1

To a solution of 3-hydroxymethylindan-1-one (1.23 g) and methyl iodide (4.31 g) in THF (20 ml) was added 55% oily sodium hydride (1.33 g) under ice-cooling, followed by stirring at the same temperature for 1 hour. To the reaction liquid was added a saturated aqueous ammonium chloride solution, followed by extraction with ethyl acetate, washed with saturated brine, and then dried over anhydrous magnesium sulfate, and the solvent was evaporated under reduced pressure. The residue was purified by silica gel column chromatography (eluent; n-hexane:ethyl acetate=10:1) to obtain a compound of Reference Example 1 as an oily substance.

Reference Example 2

To a solution of t-BuOK (3.0 g) in THF (7 ml) was added a solution of methyl 3-oxoindane-1-carboxylate (1.0 g) in THF (2 ml) at −20° C., followed by stirring at the same temperature for 30 minutes. To this was added methyl iodide (4.5 g), followed by stirring for 30 minutes while warming to room temperature. The reaction liquid was ice-cooled, and partitioned between 1 N hydrochloric acid and ethyl acetate. The organic layer was washed with saturated brine, and then dried over anhydrous magnesium sulfate, and the solvent was evaporated under reduced pressure to obtain a compound of Reference Example 2 (1.2 g) as an oily substance.

Reference Example 3

To a solution of the compound of Reference Example 2 (3.2 g) in DMSO (20 ml) was added LiCl (1.2 g), followed by stirring at 200° C. for 2 hours. After cooling the reaction, it was partitioned between 1 N hydrochloric acid and ethyl acetate, and the organic layer was washed with water and saturated brine. It was dried over anhydrous magnesium sulfate, and the solvent was then evaporated under reduced pressure. The residue was purified by silica gel column chromatography (eluent; n-hexane:ethyl acetate=4:1) to obtain a compound of Reference Example 3 (1.9 g) as an oily substance.

Reference Example 4

To a solution of the compound of Reference Example 2 (2.6 g) in methanol (30 ml) was added sodium borohydride (2.1 g) under ice-cooling, followed by heating under reflux for 30 minutes. The reaction liquid was cooled, followed by addition of a saturated aqueous ammonium chloride solution and extraction with ethyl acetate. Further, it was washed with a saturated aqueous sodium hydrogen carbonate solution and saturated brine, and then dried over anhydrous magnesium sulfate, and the solvent was evaporated under reduced pressure to obtain a compound of Reference Example 4 (2.0 g) as an oily substance.

Reference Example 5

A compound of Reference Example 5 was prepared from the compound of Reference Example 4 in the same manner as in Reference Example 1.

Reference Example 6

To a solution of the compound of Reference Example 5 (0.99 g) in methanol (8 ml) was added a 10 M aqueous sodium hydroxide solution (8 ml), followed by stirring at 60° C. for 12 hours. Methanol was evaporated under reduced pressure, and then ice-cooled, followed by addition of concentrated hydrochloric acid for neutralization and further stirring at room temperature for 1 hour. The precipitate was collected by filtration, and dried under reduced pressure to obtain a compound of Reference Example 6 (0.94 g) as a colorless amorphous substance.

Reference Example 7

To a solution of the compound of Reference Example 6 (0.94 g) and ammonium chloride (0.64 g), 1-hydroxybenzotriazole (0.54 g) in DMF (10 ml) was added N-[3-(dimethylamino)propyl]-N'-ethylcarbodiimide hydrochloride (1.2 g), followed by stirring at room temperature for 3 days. To this was added saturated aqueous ammonia solution, followed by stirring for one more day, and then the precipitate was collected by filtration, and dried under reduced pressure to obtain a compound of Reference Example 7 (0.62 g) as a colorless crystal,

Reference Example 8

The present compound was prepared from 4-methylindan-1-one in the same manner as in Reference Example 2.

Reference Example 9

The present compound was prepared from 4-trifluoromethylindan-1-one in the same manner as in Reference Example 2.

Reference Example 10

The present compound was prepared from 5-trifluoromethylindan-1-one in the same manner as in Reference Example 2.

Reference Example 11

To 3-(3-trifluoromethylphenyl)propionic acid was added trifluoromethanesulfonic acid at room temperature, followed by stirring at 60° C. for 3 hours. The reaction liquid was put into cold water, followed by extraction with a mixed solvent of ethyl acetate and THF. The organic layer was washed with saturated brine, and dried over anhydrous sodium sulfate, and the solvent was then evaporated under reduced pressure. The residue was purified by silica gel column chromatography (eluent; n-hexane:ethyl acetate=9:1 to 5:1) to obtain 5-trifluoromethylindane (2.2 g) and a compound of Reference Example 11 (0.70 g) as colorless solids, respectively.

Reference Example 12

The present compound was prepared from the compound of Reference Example 11 in the same manner as in Reference Example 2.

Reference Example 13

To a solution of 7-bromo-4-fluoro-2,2-dimethylindan-1-one (3.7 g) in toluene (30 ml) were added tributyl(vinyl) tin (7.0 g), tris(dibenzylideneacetone)dipalladium (0.40 g), and a 0.49 M solution (2.7 ml) of tri(t-butyl)phosphine in n-hexane, at followed by stirring at 70° C. for 12 hours. The reaction liquid was cooled, and a saturated aqueous potassium fluoride solution was added thereto, followed by stirring at room temperature for 30 minutes. Then, the insoluble materials were removed by filtration through Celite. The filtrate was extracted with ethyl acetate, washed with saturated brine, and then dried over anhydrous magnesium sulfate, and the solvent was evaporated under reduced pressure. The residue was purified by silica gel column chromatography (eluent; n-hexane:ethyl acetate=10:1) to obtain a compound of Reference Example 13 (1.7 g) as an oily substance.

Reference Example 14

A solution of 2-bromo-5-fluorobenzaldehyde (1.5 g), malonic acid (1.5 g), and piperidine (0.07 ml) in pyridine (10 ml) was heated for 1 day under reflux. The reaction liquid was concentrated under reduced pressure, 1 N hydrochloric acid was then added thereto for neutralization, and crystallized precipitates were collected by filtration. This was dissolved in methanol (10 ml), and a 5% rhodium carbon catalyst (150 mg) was added thereto, followed by stirring at room temperature for 12 hours under a hydrogen atmosphere (1 atm). The insoluble materials was removed by filtration through Celite, the solvent was evaporated under reduced pressure, and the residue was purified by silica gel column chromatography (eluent; chloroform:methanol=10:1) to obtain a compound of Reference Example 14 (0.50 g) as a colorless solid.

Reference Example 15

The present compound was prepared from the compound of Reference Example 14 in the same manner as in Reference Example 11.

Reference Example 16

The present compound was prepared from the compound of Reference Example 15 in the same manner as in Reference Example 1.

Reference Example 17

The present compound was prepared from 3-(3-bromo-5-methoxy phenyl)propionic acid in the same manner as in Reference Example 11.

Reference Example 18

The present compound was prepared from the compound of Reference Example 17 in the same manner as in Reference Example 2.

Reference Examples 19 to 25

The present compound was prepared from each of the corresponding indanone and a Grignard reagent in the same manner as in Reference Example 28.

Reference Example 26

The present compound was prepared from 1-bromo-2-fluorobenzene and the corresponding indanone in the same manner as in Reference Example 29.

Reference Example 27

The present compound was prepared from each of the corresponding indanone and a Grignard reagent in the same manner as in Reference Example 28.

Reference Example 28

To a solution of 2,2-dimethylindan-1-one (0.63 g) in THF was added a 1 M solution of (4-fluorophenyl)magnesium bromide in THF (7.8 ml) at room temperature, followed by stirring at the same temperature for 2 hours. To the reaction liquid was added a saturated aqueous ammonium chloride solution, followed by extraction with ethyl acetate, and the organic layer was washed with saturated brine. It was dried over anhydrous magnesium sulfate, the solvent was evaporated under reduced pressure, and the residue was purified by silica gel column chromatography (eluent; n-hexane:ethyl acetate=30:1) to obtain a compound of Reference Example 28 (0.99 g) as an oily substance.

Reference Example 29

To a solution of 2-bromoanisole (1.4 g) in diethyl ether (10 ml) was added a 1.6 M solution (4.6 ml) of n-butyl lithium in n-hexane at −78° C., followed by stirring at the same temperature for 1 hour. To this was added 2,2-dimethylindan-1-one (0.60 g), followed by further stirring at the same temperature for 1 hour. A saturated aqueous ammonium chloride solution was added thereto, followed by extraction with ethyl acetate, and the organic layer was washed with saturated brine, and dried over anhydrous magnesium sulfate. Then, the solvent was evaporated under reduced pressure. The residue was purified by silica gel column chromatography (eluent; n-hexane:ethyl acetate=30:1) to obtain a compound of Reference Example 29 (0.62 g) as an oily substance.

Reference Example 30

The present compound was prepared from each of the corresponding indanone and a Grignard reagent in the same manner as in Reference Example 28.

Reference Examples 31 and 32

The present compound was prepared from each corresponding indanone in the same manner as in Reference Example 29.

Reference Examples 33 to 41

The present compound was prepared from each corresponding indanone in the same manner as in Reference Example 42.

Reference Example 42

To a solution of 2,2,6-trimethylindan-1-one (1.8 g) in THF (35 ml) was added a 1.4 M solution (15 ml) of methyl magnesium bromide in THF/toluene (25:75), and warmed to room temperature, followed by stirring for 2 hours. After completion of the reaction, a saturated aqueous ammonium chloride solution was added thereto under ice-cooling, followed by stirring, and extracted with ethyl acetate. The organic layer was washed with saturated brine, and then dried over anhydrous sodium sulfate, and the solvent was evaporated under reduced pressure. The residue was purified by silica gel column chromatography (eluent; n-hexane:ethyl acetate=10:1) to obtain a compound of Reference Example 42 (1.9 g) as an oily substance.

Reference Example 43

To a solution of 6-methoxy-2,2-dimethylindan-1-one (2.2 g) in THF (40 ml) was added a 1.4 M solution (17 ml) of methyl magnesium bromide in THF/toluene (25:75) under ice-cooling, and warmed to room temperature, followed by stirring for 2 hours. After completion of the reaction, a saturated aqueous ammonium chloride solution was added thereto under ice-cooling, followed by stirring and extraction with ethyl acetate. The organic layer was washed with saturated brine, and then dried over anhydrous sodium sulfate, and the solvent was evaporated under reduced pressure. The residue was purified by silica gel column chromatography (eluent; n-hexane:ethyl acetate=10:1) to obtain a compound of Reference Example 43 (2.3 g) as an oily substance.

Reference Example 44

To a solution of 6-fluoro-2,2-dimethylindan-1-one (0.47 g) in THF (9 ml) was added a 0.96 M solution (5.5 ml) of methyl magnesium bromide in THF under ice-cooling, followed by warming to room temperature and stirring for 2 hours. After completion of the reaction, a saturated aqueous ammonium chloride solution was added thereto under ice-cooling, followed by stirring and extraction with ethyl acetate. The organic layer was washed with saturated brine, and then dried over anhydrous sodium sulfate, and the solvent was evaporated under reduced pressure. The residue was purified by silica gel column chromatography (eluent; n-hexane:ethyl acetate=10:1) to obtain a compound of Reference Example 44 (0.45 g) as an oily substance.

Reference Example 45

To a solution of 6-bromo-2,2-dimethylindan-1-one (3.8 g) in THF (60 ml) was added a 1.4 M solution (17 ml) of methyl magnesium bromide in THF/toluene (25:75) under ice-cooling, followed by warming to room temperature and stirring for 2 hours. After completion of the reaction, a saturated aqueous ammonium chloride solution was added thereto under ice-cooling, followed by stirring and extraction with ethyl acetate. The organic layer was washed with saturated brine, and then dried over anhydrous sodium sulfate, and the solvent was evaporated under reduced pressure. The residue was purified by silica gel column chromatography (eluent; n-hexane:ethyl acetate=5:1) to obtain a compound of Reference Example 45 (3.8 g) as an oily substance.

Reference Example 46

To a solution of 2,2-dimethyl-6-trifluoromethylindan-1-one (1.7 g) in THF (15 ml) was added a 1.4 M solution (10 ml) of methyl magnesium bromide in THF/toluene (25:75) under ice-cooling, followed by warming to room temperature and stirring for 1 hour. After completion of the reaction, a saturated aqueous ammonium chloride solution was added thereto under ice-cooling, followed by stirring and extraction with ethyl acetate. The organic layer was washed with saturated brine, and then dried over anhydrous sodium sulfate, and the solvent was evaporated under reduced pressure. The residue was purified by silica gel column chromatography (eluent; n-hexane:ethyl acetate=6:1) to obtain a compound of Reference Example 46 (1.7 g) as an oily substance.

Reference Examples 47 to 54

The present compound was prepared from the corresponding indanone in the same manner as in Reference Example 42.

Reference Example 55

To a solution of 2,2-dimethylindan-1-one (2.0 g) and trimethyl(trifluoromethyl)silane (2.7 g) in THF (20 ml) was added a 1 M solution (12 ml) of tributyl ammonium fluoride in THF under ice-cooling, followed by slowly warming to room temperature and stirring for 5 hours. 1 N hydrochloric acid was added thereto, followed by extraction with diethyl ether, washing with a saturated aqueous sodium chloride solution, and then drying over anhydrous magnesium sulfate. The solvent was evaporated under reduced pressure, and the residue was purified by silica gel column chromatography (eluent; n-hexane:ethyl acetate=10:1) to obtain a compound of Reference Example 55 (2.9 g) as an oily substance.

Reference Example 56

To a solution of 2,2-dimethylindan-1-one (2.0 g) in THF (20 ml) was added a 0.5 M solution of ethyllithium in benzene/cyclohexane (9:1) (37 ml) at −78° C., followed by stirring at the same temperature for 2 hours. To the reaction liquid was added a saturated aqueous ammonium chloride solution, followed by extraction with ethyl acetate, and drying over anhydrous sodium sulfate, and the solvent was then evaporated under reduced pressure. The residue was purified by silica gel column chromatography (eluent; n-hexane:ethyl acetate=3:1) to obtain a compound of Reference Example 56 (2.1 g) as an oily substance.

Reference Example 57

The present compound was prepared from the corresponding indanone in the same manner as in Reference Example 56.

Reference Example 58 to 61

The present compound was prepared from the corresponding indanone and Grignard reagent in the same manner as in Reference Example 42.

Example 1

2,2-Dimethyl-1-phenylindan-1-amine Monofumarate

To a solution of 2,2-dimethyl-1-phenylindan-1-ol (736 mg) in chloroform (10 ml) were added sodium azide (412 mg) and trifluoroacetic acid (1.4 ml) under ice-cooling, followed by stirring at the same temperature for 2 hours. It was alkalified by addition of 10% aqueous ammonia, and then extracted with ethyl acetate, and the organic layer was washed with saturated brine. The solvent was evaporated under reduced pressure to obtain an azide (798 mg). Thereafter, this was dissolved in methanol (10 ml), and 10% palladium/carbon (85 mg) was added thereto, followed by stirring at room temperature for 3 days under a hydrogen atmosphere (normal pressure). The reaction mixture was filtered through Celite, and the filtrate was concentrated under reduced pressure. The residue was purified by basic silica gel column chromatography (eluent; n-hexane:ethyl acetate=30:1 to 5:1) to obtain an amine (437 mg). A portion thereof (119 mg) and fumaric acid (59 mg) were dissolved in methanol, and the solvent was then evaporated under reduced pressure. The residue was recrystallized from acetone to obtain a compound of Example 1 (168 mg) as a colorless crystal.

Example 2

The present compound was prepared in the same manner as in Example 1.

Example 3 cis-3-(Methoxymethyl)-2,2-dimethyl-1-phenylindan-1-amine hydrochloride

Example 4 trans-3-Hydroxy methyl-2,2-dimethyl-1-phenylindan-1-amine hydrochloride

To a solution of the compound of Reference Example 20 (1.8 g) in methylene chloride (30 ml) were added sodium azide (1.3 g) and trifluoroacetic acid (2.5 ml), followed by stirring at the same temperature for 30 minutes. It was alkalified by addition of 10% aqueous ammonia, and extracted with ethyl acetate, and the organic layer was washed with saturated brine. The solvent was evaporated under reduced pressure to obtain an azide. Thereafter, this was dissolved in methanol (30 ml), and 10% palladium/carbon (0.5 g) was added thereto, followed by stirring at room temperature for 4 hours under a hydrogen atmosphere (normal pressure). The reaction mixture was filtered through Celite, and the filtrate was concentrated under reduced pressure. The residue was purified by silica gel column chromatography (eluent; chloroform:methanol=20:1) to obtain an amine (1.2 g). Further, a portion thereof (1.1 g) was dissolved in methylene chloride (10 ml), and a 1 M solution (4.5 ml) of boron tribromide in methylene chloride was added thereto under ice-cooling, followed by stirring for 2 hours. To the reaction liquid were added alumina and methanol, followed by stirring at room temperature for 1 hour, and the solvent was then evaporated under reduced pressure. The residue was purified by silica gel column chromatography (eluent; chloroform:methanol=4:1) to obtain free forms of the compounds of Examples 3 and 4, respectively. To each of the solutions in ethyl acetate was added a 4 N solutions of HCl in ethyl acetate, and the solvent was then evaporated under reduced pressure. The residue was crystallized from n-hexane to obtain a compound of Example 3 (350 mg), and a compound of Example 4 (97 mg) as colorless crystals, respectively.

Example 5 trans-2-Methyl-1,2-diphenylindan-1-amine Hydrochloride

Example 6 cis-2-Methyl-1,2-diphenylindan-1-amine hydrochloride

A hydrochloride of a diastereomer mixture obtained in the same manner as in Example 17 from 1,2-diphenylindan-1-ol was recrystallized from ethanol to obtain a compound of Example 5, and further, the filtrate was concentrated under reduced pressure, and then was purified by alumina/silica gel column chromatography (eluent; chloroform). Thus obtained residue was crystallized from n-hexane to make its hydrochloride by an ordinary method, thereby obtaining a compound of Example 6 as a colorless crystal, respectively.

Examples 7 and 8

The present compounds were prepared in the same manner as in Example 1.

Example 9

The present compound was prepared in the same manner as in Example 21.

Example 10

N,2,2-trimethyl-1-phenylindan-1-amine hydrochloride

To a solution of a desalted compound of Example 1 (125 mg) in ethanol (5 ml) were added an aqueous 37% formaldehyde solution (0.2 ml) and 10% palladium/carbon, followed by stirring at room temperature for 1 day under a hydrogen atmosphere (normal pressure). The reaction mixture was filtered through Celite, and the filtrate was concentrated under reduced pressure, and then partitioned between a saturated aqueous sodium hydrogen carbonate solution and ethyl acetate. The organic layer was washed with saturated brine, and dried over anhydrous magnesium sulfate, and the solvent was evaporated under reduced pressure. The residue was purified by basic silica gel column chromatography (eluent; n-hexane:ethyl acetate=20:1 to 5:1). Then, the residue was dissolved in a 4 N solution of HCl in ethyl acetate, and the solvent was evaporated under reduced pressure. The residue was washed with a mixed solvent of diisopropyl ether and 1,4-dioxane to obtain a compound of Example 10 (115 mg) as a colorless crystal.

Example 11

The present compound was prepared by reacting for a longer time in the same manner as in Example 10.

Examples 12 to 16

The present compounds were prepared in the same manner as in Example 17.

Example 17

1-(4-Fluorophenyl)-2,2-dimethylindan-1-amine monofumarate

To a solution of the compound of Reference Example 28 (984 mg) in chloroform (12 ml) were added sodium azide (500 mg) and trifluoroacetic acid (1.7 ml) under ice-cooling, followed by stirring at room temperature for 3 hours. It was alkalified by addition of 10% aqueous ammonia, and extracted with chloroform, and then the organic layer was washed with saturated brine. It was dried over anhydrous magnesium sulfate, and the solvent was then evaporated under reduced pressure. The residue was purified by silica gel column chromatography (eluent; n-hexane:ethyl acetate=40:1) to obtain an azide (1.08 g). Thereafter, this was dissolved in methanol (13 ml), and 10% palladium/carbon (102 mg) was added thereto, followed by stirring at room temperature for 3 hours under a hydrogen atmosphere (normal pressure). The reaction mixture was filtered through Celite, and the filtrate was concentrated under reduced pressure. The residue was purified by basic silica gel column chromatography (eluent; n-hexane:ethyl acetate=30:1 to 5:1) to obtain an amine (562 mg). A portion thereof (100 mg) and fumaric acid (51 mg) were dissolved in methanol, and the solvent was then evaporated under reduced pressure. The residue was washed with a mixed solvent of diisopropyl ether and 1,4-dioxane to obtain a compound of Example 17 (127 mg) as a colorless crystal.

Example 18

1-(2-Methoxy phenyl)-2,2-dimethylindan-1-amine hydrochloride

To a solution of the compound of Reference Example 29 (620 mg) in chloroform (9 ml) were added sodium azide (304 mg) and trifluoroacetic acid (1 ml) under ice-cooling, followed by stirring at room temperature for 3 hours. It was alkalified by addition of 10% aqueous ammonia, and then extracted with chloroform, and the organic layer was washed with saturated brine. It was dried over anhydrous sodium sulfate, and the solvent was then evaporated under reduced pressure. The residue was purified by silica gel column chromatography (eluent; n-hexane:ethyl acetate=30:1) to obtain an azide (635 mg). Thereafter, this was dissolved in methanol (8 ml), and 10% palladium/carbon (62 mg) was added thereto, followed by stirring at room temperature for 3 hours under a hydrogen atmosphere (normal pressure). The reaction mixture was filtered through Celite, and the filtrate was concentrated under reduced pressure. The residue was purified by silica gel column chromatography (eluent; chloroform:methanol=30:1) to obtain an amine (357 mg). Further, this was dissolved in ethyl acetate, a 4 N solution of HCl in ethyl acetate was added thereto, and the solvent was evaporated under reduced pressure. The residue was washed with n-hexane to obtain a compound of Example 18 (231 mg) as a colorless crystal.

Examples 19 and 20

The present compounds were prepared in the same manner as in Example 18.

Example 21

1-(3-Hydroxyphenyl)-2,2-dimethylindan-1-amine

To a solution of the compound of Example 19 (150 mg) in methylene chloride (2 ml) was added a 1 M solution of boron tribromide in methylene chloride (0.67 ml) under ice-cooling, followed by stirring for 2 hours. A saturated aqueous sodium hydrogen carbonate solution was added thereto, followed by extraction with chloroform, and drying over anhydrous magnesium sulfate, and the solvent was then evaporated under reduced pressure. The residue was purified by basic silica gel column chromatography (eluent; n-hexane:ethyl acetate=1:1 to 0:1) to obtain a compound of Example 21 (51 mg) as a colorless amorphous substance.

Example 22

The present compound was prepared in the same manner as in Example 18.

Example 23

1,2,2-Trimethylindan-1-amine hydrochloride

To a solution of 1,2,2-trimethylindan-1-ol (406 mg) in chloroform (6 ml) were added sodium azide (300 mg) and trifluoroacetic acid (1 ml) under ice-cooling, followed by stirring at room temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide. Then, this was dissolved in methanol (6 ml), and 10% palladium-carbon (40 mg) was added thereto, followed by stirring at room temperature for 3 hours under a hydrogen atmosphere (normal pressure). The reaction mixture was filtered through Celite, and the filtrate was concentrated under reduced pressure. The residue was purified by basic silica gel column chromatography (eluent; n-hexane:ethyl acetate=30:1 to 5:1) to obtain an amine (140 mg) as an oily substance. Further, this was dissolved in ethyl acetate, a 4 N solution of HCl in ethyl acetate was added thereto, and the solvent was evaporated under reduced pressure. The residue was crystallized from diisopropyl ether to obtain a compound of Example 23 (153 mg) as a colorless crystal.

Example 24 cis-1,2,2,3-Tetramethylindan-1-amine hydrochloride

Example 25 trans-1,2,2,3-Tetramethylindan-1-amine hydrochloride

The same procedure as in Example 23 using the compound of Reference Example 33 was carried out, and the resulting diastereomer was separated, and purified by silica gel column chromatography (eluent; chloroform:methanol: saturated aqueous ammonia=50:1:0.1 to 20:1:0.1), and each was made into its hydrochloride by an ordinary method, thereby obtaining a compound of Example 24, and a compound of Example 25 as colorless crystals, respectively.

Example 26

The present compound was prepared in the same manner as in Example 23.

Example 27 cis-3-Methoxy-1,2,2-trimethylindan-1-amine hydrochloride

To a 3 N aqueous solution (10 ml) of sodium hydroxide were added bromine (0.18 ml) and the compound of Reference Example 7 (0.62 g) under ice-cooling, followed by stirring at room temperature for 3 days. An aqueous $Na_2SO_3$ solution was added thereto, followed by stirring, extraction with methylene chloride, and washing with saturated brine. It was dried over anhydrous magnesium sulfate, and the solvent was then evaporated under reduced pressure. The residue was purified by basic silica gel column chromatography (eluent; n-hexane:ethyl acetate=4:1), and thereafter, by neutral silica gel column chromatography (eluent; chloroform:methanol: saturated brine=50:1:0.1) to obtain an amine (179 ml) as an oily substance. This was made into its hydrochloride, and then crystallized from n-hexane to obtain a compound of Example 27 (89 mg) as a colorless crystal.

Example 28

1,2,2,4-Tetramethylindan-1-amine hydrochloride

Example 29

4-Fluoro-1,2,2-trimethylindan-1-amine hydrochloride

Example 30

4-Trifluoromethyl-1,2,2-trimethylindan-1-amine hydrochloride

Example 31

1,2,2,5-Tetramethylindan-1-amine hydrochloride

Example 32

5-Methoxy-1,2,2-trimethylindan-1-amine hydrochloride

Example 33

5-Fluoro-1,2,2-trimethylindan-1-amine hydrochloride

Example 34V

5-Chloro-1,2,2-trimethylindan-1-amine hydrochloride

Example 35

5-Trifluoromethyl-1,2,2-trimethylindan-1-amine hydrochloride

The compounds of Examples 28 to 35 as described above were prepared from the corresponding alcohols in the same manner as in Example 23.

Example 36

1,2,2,6-Tetramethylindan-1-amine hydrochloride

To a solution of the compound of Reference Example 42 (1.9 g) in chloroform (38 ml) were added sodium azide (1.3 g) and trifluoroacetic acid (4.6 mg) under ice-cooling, followed by stirring at the same temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide. Then, this was dissolved in methanol (38 ml), and 10% palladium-carbon (200 mg) was added thereto, followed by stirring at room temperature for 12 hours under a hydrogen atmosphere (normal pressure). The reaction mixture was filtered through Celite, and the filtrate was concentrated under reduced pressure. The residue was purified by silica gel column chromatography (eluent; chloroform: methanol=10:1) to obtain an amine (720 mg) as an oily substance. Further, this was dissolved in ethyl acetate, a 4 N HCl solution in ethyl acetate was added thereto, and the solvent was evaporated under reduced pressure. The residue was crystallized from n-hexane/diethylether to obtain a compound of Example 36 (227 mg) as a colorless crystal.

Example 37

6-Hydroxy-1,2,2-trimethylindan-1-amine hydrochloride

To a solution of a free form (96 mg) of the compound of Example 38 in 1,2-dichloroethane (2 ml) was added a 1 M boron tribromide solution in methylene chloride (0.5 ml) under ice-cooling, followed by stirring at room temperature for 3 hours. To the reaction liquid was slowly added water under ice-cooling and stirred, followed by extraction with ethyl acetate, and then washing with saturated brine. It was dried over anhydrous magnesium sulfate, and the solvent was then evaporated under reduced pressure. The residue was recrystallized from diisopropyl ether to obtain an amine (48 mg) as a colorless crystal. Further, this was made into its hydrochloride by an ordinary method, and then crystallized from a mixed solvent of diethylether and n-hexane to obtain a compound of Example 37 (47 mg) as a colorless crystal.

Example 38

6-Methoxy-1,2,2-trimethylindan-1-amine hydrochloride

To a solution of the compound of Reference Example 43 (2.3 g) in chloroform (40 ml) were added sodium azide (1.4 g) and trifluoroacetic acid (4.8 ml) under ice-cooling, followed by stirring at the same temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide. Then, this was dissolved in methanol (25 ml), and 10% palladium-carbon (330 mg) was added thereto, followed by stirring at room temperature for 12 hours under a hydrogen atmosphere (normal pressure). The reaction mixture was filtered through Celite, and the filtrate was concentrated under reduced pressure. The residue was purified by silica gel column chromatography (eluent; chloroform: methanol=10:1) to obtain an amine (1.1 g) as an oily substance. Further, a portion thereof (270 mg) was made into its hydrochloride by an ordinary method, and recrystallized from a mixed solvent of diethylether and ethyl acetate to obtain a compound of Example 38 (107 mg) as a colorless crystal.

Example 39

The present compound was prepared in the same manner as in Example 40.

Example 40

6-Isopropoxy-1,2,2-trimethylindan-1-amine hydrochloride

To a solution of a free form (179 mg) of the compound of Example 37 in THF (3 ml) were added 2-propanol (5 ml), diethylazodicarboxylate (0.55 ml), and triphenylphosphine (300 mg), followed by stirring at room temperature for 1 day. The reaction liquid was concentrated under reduced pressure, and then partitioned between ethyl acetate and 1 N hydrochloric acid. The aqueous layer was neutralized with a 1 N aqueous sodium hydroxide solution, followed by extraction with ethyl acetate, washed with saturated brine, and then dried over anhydrous magnesium sulfate. The solvent was evaporated under reduced pressure. The residue was purified by basic silica gel column chromatography (eluent; n-hexane:ethyl acetate=10:1) to obtain an isopropoxy derivative (171 mg) as an oily substance. This was made into its hydrochloride by an ordinary method, and then crystallized from diethylether to obtain a compound of Example 40 (128 mg) as a colorless crystal.

Example 41

6-Fluoro-1,2,2-trimethylindan-1-amine hydrochloride

To a solution of a compound of Reference Example 44 (444 mg) in chloroform (8 ml) were added sodium azide (300 mg) and trifluoroacetic acid (1 ml) under ice-cooling, followed by stirring at room temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide. Then, this was dissolved in methanol (6 ml), and 10% palladium-carbon (80 mg) was added thereto, followed by stirring at room temperature for 3 hours under a hydrogen atmosphere (normal pressure). The reaction mixture was filtered through Celite, and the filtrate was concentrated under reduced pressure. The residue was purified by basic silica gel column chromatography (eluent; n-hexane:ethyl acetate=1:1) to obtain an amine (327 mg) as an oily substance. Further, this was dissolved in ethyl acetate, a 4 N HCl solution in ethyl acetate was added thereto, and the solvent was evaporated under reduced pressure. The residue was crystallized from diethylether to obtain a compound of Example 41 (310 mg) as a colorless crystal.

Example 42

6-Bromo-1,2,2,-trimethylindan-1-amine hydrochloride

To a solution of a compound of Example 45 (3.8 g) in chloroform (60 ml) were added sodium azide (1.9 g) and trifluoroacetic acid (3.4 ml) under ice-cooling, followed by stirring at the same temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide. Then, this was dissolved in methanol (50 ml), and triphenylphosphine (7.8 g) was added thereto, followed by heating under reflux for 1 day.

Since the reaction was not completed, tributylphosphine (3.0 g) was further added thereto, followed by stirring at room temperature for 3 hours, and then the reaction liquid was concentrated under reduced pressure. The residue was purified by silica gel column chromatography (eluent; chloroform:methanol=10:1) to obtain an amine (1.2 g) as an oily substance. Further, a portion thereof (204 mg) was made into its hydrochloride by an ordinary method, and recrystallized from ethyl acetate to obtain a compound of Example 42 (222 mg) as a colorless crystal.

Example 43

6-Trifluoromethyl-1,2,2-trimethylindan-1-amine hydrochloride

To a solution of a compound of Example 46 (1.6 mg) in methylene chloride (20 ml) were added sodium azide (0.85 g) and trifluoroacetic acid (2.5 ml) under ice-cooling, followed by stirring at the same temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide. Then, this was dissolved in methanol (100 ml), and 10% palladium-carbon (0.5 g) was added thereto, followed by stirring at room temperature for 15 hours under a hydrogen atmosphere (normal pressure). The reaction mixture was filtered through Celite, and the filtrate was concentrated under reduced pressure. The residue was partitioned between 1 N hydrochloric acid and ethyl acetate, and the aqueous layer was alkalified with sodium hydrogen carbonate, extracted with ethyl acetate, washed with water and saturated brine, and then dried over anhydrous magnesium sulfate, and the solvent was evaporated under reduced pressure to obtain an amine (1.1 g) as an oily substance. Further, this was made into its hydrochloride by an ordinary method, and then crystallized from a mixed solvent of n-hexane and diethylether to obtain a compound of Example 43 (1.1 g) as a colorless crystal.

Example 44

6-Cyano-1,2,2-trimethylindan-1-amine hydrochloride

To a solution of a free form of the compound of Example 42 (112 mg) in N-methylpyrrolidone were added zinc cyanide (63 mg), calcium hydroxide (40 mg) and tetrakis(triphenylphosphine)palladium (150 mg), followed by stirring under heat at 110° C. for 1 day. The reaction liquid was cooled, and then ethyl acetate and water were added thereto, followed by stirring. The insoluble materials were removed by filtration through Celite. The filtrate was separated out, and the organic layer was washed with saturated brine, and dried over anhydrous sodium sulfate, and the solvent was then evaporated under reduced pressure. The residue was purified by silica gel chromatography (eluent; chloroform:methanol=10:1) to obtain a cyano derivative form (78 mg) as an oily substance. Further, this was made into its hydrochloride by an ordinary method, and crystallized from ethyl acetate to obtain a compound of Example 44 (79 mg) as a colorless crystal.

Example 45

1,2,2-Trimethyl-6-vinylindan-1-amine hydrochloride

To a solution of a free form of the compound of Example 42 (0.67 g) in toluene (7 ml) were added tributyl(vinyl)tin (1.3 g), tris(dibenzylideneacetone)dipalladium (0.15 g) and tri(t-butyl)phosphine (0.32 g), followed by stirring under heat at 70° C. for 2 hours. An aqueous potassium fluoride solution was added thereto, followed by stifling for 1 hour, and the insoluble materials were removed by filtration through Celite. The filtrate was extracted with ethyl acetate, washed with saturated brine, and dried over anhydrous sodium sulfate, and the solvent was then evaporated under reduced pressure. The residue was purified by silica gel column chromatography (eluent; n-hexane:ethyl acetate=8:1) to obtain an amine (349 mg) as an oily substance. Further, a portion thereof (157 mg) was made into its hydrochloride by an ordinary method, and crystallized from n-hexane to obtain a compound of Example 45 (38 mg) as a colorless crystal.

Example 46

1,2,2-Trimethyl-6-(piperidin-1-yl)indan-1-amine hydrochloride

To a solution of a free form of the compound of Example 42 (144 mg) in toluene (3 ml) were added piperidine (0.07 ml), palladium diacetate (7 mg), sodium t-butoxide (81 mg), and tri(2-methylphenyl)phosphine (18 mg), followed by stirring under heat at 80° C. for 1 day. The reaction liquid was cooled, and then partitioned between ethyl acetate and water, and the organic layer was washed saturated brine. It was dried over anhydrous sodium sulfate, and the solvent was then evaporated under reduced pressure. The residue was purified by basic silica gel column chromatography (eluent; chloroform:methanol=10:1) to obtain an amine (75 mg) as an oily substance. Further, this was made into its dihydrochloride by an ordinary method, and crystallized from ethyl acetate to obtain a compound of Example 46 (61 mg) as a colorless crystal.

Example 47

The present compound was prepared from compound of Example 47 in the same manner as in Example 41.

Example 48

7 Fluoro-1,2,2-trimethylindan-1-amine hydrochloride

To a solution of the compound of Reference Example 51 (774 mg) in chloroform (15 ml) were added sodium azide (370 mg) and trifluoroacetic acid (1.3 ml) under ice-cooling, followed by stirring at the same temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide (700 g). Then, a portion thereof (480 mg) was dissolved in methanol (10 ml), and 10% palladium-carbon (50 mg) was added thereto, followed by stirring at room temperature for 1 day under a hydrogen atmosphere (normal pressure). The reaction mixture was filtered through Celite, and the filtrate was concentrated under reduced pressure to obtain an oily substance. This was made into its hydrochloride by an ordinary method, and crystallized from ethyl acetate to obtain a compound of Example 48 (55 mg) as a colorless crystal.

Example 49

The present compound was prepared in the same manner as in Example 41.

Example 50

The present compound was prepared in the same manner as in Example 42.

Example 51

7-Ethyl-4-fluoro-1,2,2-trimethylindan-1-amine hydrochloride

To a solution of a free form of the compound of Example 52 (79 mg) in methanol (20 ml) was added 10% palladium-carbon (50 mg), followed by stirring at room temperature for 12 hours under a hydrogen atmosphere (normal pressure). The insoluble materials were removed by filtration through Celite, and the solvent was then evaporated under reduced pressure. The residue was purified by silica gel column chromatography (eluent; chloroform:methanol=10:1) and then made into its hydrochloride by an ordinary method to obtain a compound of Example 51 (53 mg) as a pale yellow amorphous substance.

Examples 52 and 53

The present compounds were prepared in the same manner as in Example 43.

Example 54

The present compound was prepared in the same manner as in Example 41.

Example 55

The present compound was prepared in the same manner as in Example 42.

Example 56

The present compound was prepared in the same manner as in Example 41.

Example 57

2,2-Dimethyl-1-trifluoromethylindan-1-amine hydrochloride

To a solution of the compound of Example 55 (2.3 g) in chloroform (30 ml) were added sodium azide (1.3 g) and concentrated sulfuric acid (1.6 ml) under ice-cooling, followed by stifling at room temperature for 2 hours. The reaction solution was further ice-cooled, and 10% aqueous ammonia was added thereto, followed by stirring and extraction with chloroform. The organic layer was washed with saturated brine, and then dried over anhydrous sodium sulfate, and the solvent was evaporated under reduced pressure. The residue was dissolved in methanol (20 ml), and 10% palladium-carbon (200 mg) was added thereto, followed by stirring at room temperature for 12 hours under a hydrogen atmosphere (normal pressure). The insoluble materials were removed by filtration through Celite, and the solvent was evaporated under reduced pressure. The residue was dissolved in ethyl acetate, followed by extraction with 1 M hydrochloric acid. The aqueous layer was alkalified with 1 M sodium hydroxide, and extracted with ethyl acetate. It was washed with saturated brine, and dried over anhydrous sodium sulfate, and the solvent was evaporated under reduced pressure to obtain an amine (1.17 g). This was made into its hydrochloride by an ordinary method, and then crystallized from a mixed solvent of diethylether and ethyl acetate to obtain a compound of Example 57 (234 mg) as a colorless crystal.

Example 58

1-Ethyl-2,2-dimethylindan-1-amine hydrochloride

To a solution of a compound of Reference Example 56 (606 mg) in chloroform (9 ml) were added sodium azide (414 mg) and trifluoroacetic acid (1.4 ml) under ice-cooling, followed by stirring at room temperature for 1 hour. It was alkalified by addition of 10% aqueous ammonia, and then extracted with chloroform, and the organic layer was washed with saturated brine. It was dried over anhydrous magnesium sulfate, and the solvent was then evaporated under reduced pressure to obtain an azide. Then, this was dissolved in methanol (9 ml), and 10% palladium-carbon (700 mg) was added thereto, followed by stirring at room temperature for 3 hours under a hydrogen atmosphere (normal pressure). The reaction mixture was filtered through Celite, and the filtrate was concentrated under reduced pressure. The residue was purified by basic silica gel column chromatography (eluent; n-hexane:ethyl acetate=5:1) to obtain an amine (339 mg) as an oily substance. Further, this was made into its hydrochloride by an ordinary method, and then crystallized from diisopropyl ether to obtain a compound of Example 58 (190 mg) as a colorless crystal.

Example 59

The present compound was prepared in the same manner as in Example 58.

Example 60

1-Isopropyl-2,2-dimethylindan-1-amine hydrochloride

To a solution of 1-isopropyl-2,2-dimethylindan-1-ol (175 mg) in chloroform (3 ml) were added sodium azide (114 mg) and trifluoroacetic acid (0.4 ml) under ice-cooling, followed by stirring at room temperature for 3 days. It was alkalified by addition of 10% aqueous ammonia, and then extracted with chloroform, and the organic layer was washed with saturated brine. It was dried over anhydrous magnesium sulfate, and the solvent was then evaporated under reduced pressure. The residue was purified by silica gel column chromatography (eluent; n-hexane:ethyl acetate=30:1) to obtain an azide (106 mg) as an oily substance. Then, this was dissolved in methanol (3 ml), and 10% palladium-carbon (15 mg) was added thereto, followed by stifling at room temperature for 1 day under a hydrogen atmosphere (normal pressure). The reaction mixture was filtered through Celite, and the solvent was evaporated under reduced pressure to obtain an amine (71 mg) as an oily substance. Further, a portion thereof (20 mg) was made into its hydrochloride by an ordinary method, and crystallized from diisopropyl ether to obtain a compound of Example 60 (16 mg) as a colorless crystal.

Examples 61 to 63

The present compound was prepared in the same manner as in Example 60.

Example 64 trans-2-Ethyl-1,2-dimethylindan-1-amine hydrochloride

Example 65 cis-2-Ethyl-1,2-dimethylindan-1-amine hydrochloride

The same procedure as in Example using the compound of Reference Example 60 was carried out, and the resulting diastereomer was separated and purified by basic silica gel column chromatography (eluent; n-hexane:ethyl acetate=20:1 to 10:1), and the resulting amine was made into its hydrochloride by an ordinary method, thereby obtaining a compound of Example 64 and a compound of Example 65, as colorless amorphous substances, respectively.

Example 66

1'-Methyl-1',3'-dihydrospiro[cyclopropan-1,2'-inden]-1'-amine hydrochloride

Example 67

1'-Methyl-1',3'-dihydrospiro[cyclopentan-1,2'-inden]-1'-amine hydrochloride

The present compound was prepared in the same manner as in Example 58.

Examples 68 and 69

The present compounds were prepared in the same manner as in Example 58.

The structural formulae and the physicochemical data of the compounds of the above Reference Examples and the compounds of the above Examples are shown in the following Tables 2 to 14. The compounds shown in Table 15 may be readily produced similarly to the above Examples or Production Processes or according to the modifications apparent to one skilled in the art. The symbols in the Tables have the following meanings.

Rf.: Reference Example, Ex.: Example, STRUCTURE: structural formula, DATA: data, SALT: salt, Ph: phenyl, Me: methyl, Et: ethyl, OMe: methoxy, thienyl: thienyl, iPr: isopropyl, vinyl: vinyl, 1-Pip: 1-piperidinyl, n-Bu: normal butyl, c-Hex: cyclohexyl, c-Pr: cyclopropyl, c-Pn: cyclopentyl, Bn: benzyl, NMR: nuclear magnetic resonance spectrum (TMS internal standard), MS: mass spectrometry, fumarate: fumaric acid, HCl salt: hydrochloride, 2HCl salt: 2hydrochloride, free base: a free form

TABLE 2

| Rf. | STRUCTURE | DATA |
|---|---|---|
| 1 | 2,2-dimethyl-3-(methoxymethyl)indan-1-one | FAB-MS (m/z); 205 [(M + 1)$^+$] |
| 2 | methyl 1,2,2-trimethyl-3-oxo-2,3-dihydro-1H-indene-1-carboxylate | EI-MS (m/z); 232 [M$^+$] |
| 3 | 2,2,3-trimethylindan-1-one | EI-MS (m/z); 174 [M$^+$] |
| 4 | methyl 3-hydroxy-1,2,2-trimethyl-2,3-dihydro-1H-indene-1-carboxylate | EI-MS (m/z); 234 [M$^+$] |
| 5 | methyl 3-methoxy-1,2,2-trimethyl-2,3-dihydro-1H-indene-1-carboxylate | EI-MS (m/z); 248 [M$^+$] |
| 6 | 3-methoxy-1,2,2-trimethyl-2,3-dihydro-1H-indene-1-carboxylic acid | EI-MS (m/z); 234 [M$^+$] |
| 7 | 3-methoxy-1,2,2-trimethyl-2,3-dihydro-1H-indene-1-carboxamide | FAB-MS (m/z); 234 [M + 1)$^+$] |
| 8 | 2,2,4-trimethylindan-1-one | EI-MS (m/z); 174 [M$^+$] |

TABLE 2-continued

| Rf. | STRUCTURE | DATA |
|---|---|---|
| 9 | 2,2-dimethyl-4-(trifluoromethyl)indan-1-one | EI-MS (m/z); 228 [M$^+$] |
| 10 | 2,2-dimethyl-5-(trifluoromethyl)indan-1-one | EI-MS (m/z); 228 [M$^+$] |
| 11 | 7-(trifluoromethyl)indan-1-one | EI-MS (m/z); 200 [M$^+$] |
| 12 | 2,2-dimethyl-7-(trifluoromethyl)indan-1-one | EI-MS (m/z); 200 [M$^+$] |

TABLE 3

| Rf. | STRUCTURE | DATA |
|---|---|---|
| 13 | 4-fluoro-2,2-dimethyl-7-vinylindan-1-one | EI-MS (m/z); 204 [M$^+$] |
| 14 | 3-(2-bromo-5-fluorophenyl)propanoic acid | FAB-MS (m/z); 245, 247 [(M − 1)$^+$] |

TABLE 3-continued

| Rf. | STRUCTURE | DATA |
|---|---|---|
| 15 | 4-Br-7-F-indan-1-one | EI-MS (m/z); 228, 230 [M+] |
| 16 | 4-Br-7-F-2,2-dimethyl-indan-1-one | EI-MS (m/z); 256, 258 [M+] |
| 17 | 7-Br-5-MeO-indan-1-one | EI-MS (m/z); 240, 242 [M+] |
| 18 | 7-Br-5-MeO-2,2-dimethyl-indan-1-one | FAB-MS (m/z); 269, 271 [(M + 1)+] |

TABLE 4

[Structure: indanol with R1 (with HO), R2, R3 at 2-position; R4, R5 at 3-position; R6, R7, R8, R9 on aromatic ring]

| Rf. | R$^1$ | R$^2$, R$^3$ | R$^4$, R$^5$ | R$^6$/R$^7$/R$^8$/R$^9$ | DATA |
|---|---|---|---|---|---|
| 19 | Ph | Et, Et | H, H | H/H/H/H | EI-MS (m/z); 266 [M+] |
| 20 | Ph | Me, Me | CH$_2$OMe, H | H/H/H/H | FAB-MS (m/z); 281 [(M − 1)+] |
| 21 | Ph | Me, Me | H, H | H/H/Me/H | EI-MS (m/z); 252 [M+] |
| 22 | Ph | Me, Me | H, H | H/H/OMe/H | FAB-MS (m/z); 267 [(M − 1)+] |
| 23 | 2-Me-Ph | Me, Me | H, H | H/H/H/H | EI-MS (m/z); 252 [M+] |
| 24 | 3-Me-Ph | Me, Me | H, H | H/H/H/H | NMR(CDCl$_3$): 0.65(3H, s), 1.20(3H, s), 2.35(3H, s) ppm. |
| 25 | 4-Me-Ph | Me, Me | H, H | H/H/H/H | ESI-MS (m/z); 235 [(M − 17)+] |
| 26 | 2-F-Ph | Me, Me | H, H | H/H/H/H | EI-MS (m/z); 256 [M+] |
| 27 | 3-F-Ph | Me, Me | H, H | H/H/H/H | FAB-MS (m/z); 239 [(M − 17)+] |
| 28 | 4-F-Ph | Me, Me | H, H | H/H/H/H | EI-MS (m/z); 256 [M+] |
| 29 | 2-OMe-Ph | Me, Me | H, H | H/H/H/H | EI-MS (m/z); 268 [M+] |
| 30 | 3-OMe-Ph | Me, Me | H, H | H/H/H/H | NMR(CDCl$_3$): 0.67(3H, s), 1.20(3H, s),, 3.79(3H, s) ppm. |
| 31 | 4-OMe-Ph | Me, Me | H, H | H/H/H/H | FAB-MS (m/z); 251 [(M − 17)+] |
| 32 | 2-thienyl | Me, Me | H, H | H/H/H/H | EI-MS (m/z); 227 [(M − 17)+] |
| 33 | Me | Me, Me | Me, H | H/H/H/H | EI-MS (m/z); 190 [M+] |
| 34 | Me | Me, Me | Me, Me | H/H/H/H | EI-MS (m/z); 204 [M+] |
| 35 | Me | Me, Me | H, H | Me/H/H/H | EI-MS (m/z); 190 [M+] |
| 36 | Me | Me, Me | H, H | F/H/H/H | EI-MS (m/z); 194 [M+] |
| 37 | Me | Me, Me | H, H | CF$_3$/H/H/H | EI-MS (m/z); 244 [M+] |

TABLE 5

| Rf. | R$^1$ | R$^2$, R$^3$ | R$^4$, R$^5$ | R$^6$/R$^7$/R$^8$/R$^9$ | DATA |
|---|---|---|---|---|---|
| 38 | Me | Me, Me | H, H | H/Me/H/H | EI-MS (m/z); 190 [M+] |
| 39 | Me | Me, Me | H, H | H/F/H/H | EI-MS (m/z); 194 [M+] |
| 40 | Me | Me, Me | H, H | H/Cl/H/H | ESI-MS (m/z); 193 [M+ − 17] |
| 41 | Me | Me, Me | H, H | H/CF$_3$/H/H | EI-MS (m/z); 244 [M+] |
| 42 | Me | Me, Me | H, H | H/H/Me/H | EI-MS (m/z); 290 [M+] |
| 43 | Me | Me, Me | H, H | H/H/OMe/H | EI-MS (m/z); 206 [M+] |
| 44 | Me | Me, Me | H, H | H/H/F/H | EI-MS (m/z); 194 [M+] |
| 45 | Me | Me, Me | H, H | H/H/Br/H | EI-MS (m/z); 254, 256 [M+] |
| 46 | Me | Me, Me | H, H | H/H/CF$_3$/H | EI-MS (m/z); 244 [M+] |
| 47 | Me | Me, Me | H, H | H/H/H/Me | EI-MS (m/z); 190 [M+] |
| 48 | Me | Me, Me | H, H | H/H/H/CF$_3$ | EI-MS (m/z); 244 [M+] |
| 49 | Me | Me, Me | H, H | F/H/H/Br | NMR(CDCl$_3$): 1.18(3H, s), 1.43(3H, s) ppm. |
| 50 | Me | Me, Me | H, H | F/H/H/vinyl | EI-MS (m/z); 220 [M+] |
| 51 | Me | Me, Me | H, H | Br/H/H/F | EI-MS (m/z); 272, 274 [M+] |

TABLE 5-continued

| Rf. | R¹ | R², R³ | R⁴, R⁵ | R⁶/R⁷/R⁸/R⁹ | DATA |
|---|---|---|---|---|---|
| 52 | Me | Me, Me | H, H | H/OMe/OMe/H | ESI-MS (m/z); 259 [M⁺ + 23] |
| 53 | Me | Me, Me | H, H | H/OMe/H/Br | EI-MS (m/z); 284, 286 [M⁺] |
| 54 | Me | Me, Me | H, H | H/H/F/OMe | ESI-MS (m/z); 247 [M⁺ + 23] |
| 55 | $CF_3$ | Me, Me | H, H | H/H/H/H | EI-MS (m/z); 230 [M⁺] |
| 56 | Et | Me, Me | H, H | H/H/H/H | EI-MS (m/z); 173 [M⁺ − 17] |
| 57 | Et | Me, Me | H, H | Me/H/H/H | NMR(DMDO-$d_6$): 0.80(3H, t), 0.87(3H, s), 1.06(3H, s) ppm. |
| 58 | c-Hex | Me, Me | H, H | H/H/H/H | FAB-MS (m/z); 245 [M⁺ + 1] |
| 59 | Bn | Me, Me | H, H | H/H/H/H | EI-MS (m/z); 235 [M⁺ − 17] |
| 60 | Me | Me, Et | H, H | H/H/Me/H | EI-MS (m/z); 204 [M⁺] |
| 61 | Me | Me, c-Pn | H, H | H/H/H/H | EI-MS (m/z); 202 [M⁺] |

TABLE 6

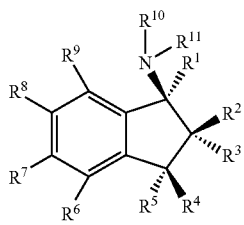

| Ex. | R¹ | R²/R³ | R⁴/R⁵ | R⁶/R⁷/R⁸/R⁹ | R¹⁰/R¹¹ | DATA |
|---|---|---|---|---|---|---|
| 1 | Ph | Me/Me | H/H | H/H/H/H | H/H | [fumarate] FAB-MS(m/z); 238 [(M + 1)⁺] ¹H NMR(DMSO-d6): 0.60(3H, s), 1.10(3H, s), 2.66(1H, d, J = 15.7Hz), 2.81(1H, d, J = 15.7 Hz), 6.53(2H, s), 7.12(2H, d, J = 7.33 Hz), 7.22-7.35 (7H, m). |
| 2 | Ph | Et/Et | H/H | H/H/H/H | H/H | [fumarate] FAB-MS(m/z); 266 [(M + 1)⁺] |
| 3 | Ph | Me/Me | CH₂OMe/H | H/H/H/H | H/H | [HCl salt] FAB-MS(m/z); 282 [(M + 1)⁺] |

TABLE 6-continued

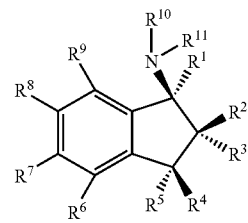

| Ex. | R¹ | R²/R³ | R⁴/R⁵ | R⁶/R⁷/R⁸/R⁹ | R¹⁰/R¹¹ | DATA |
|---|---|---|---|---|---|---|
| 4 | Ph | Me/Me | CH₂OH/H | H/H/H/H | H/H | [HCl salt] FAB-MS(m/z); 268 [(M + 1)⁺] |
| 5 | Ph | Me/Ph | H/H | H/H/H/H | H/H | [HCl salt] FAB-MS(m/z); 300 [(M + 1)⁺] |
| 6 | Ph | Ph/Me | H/H | H/H/H/H | H/H | [HCl salt] FAB-MS(m/z); 300 [(M + 1)⁺] |
| 7 | Ph | Me/Me | H/H | H/H/Me/H | H/H | [fumarate] FAB-MS(m/z); 252 [(M + 1)⁺] |
| 8 | Ph | Me/Me | H/H | H/H/OMe/H | H/H | [freebase] FAB-MS(m/z); 251 [(M − 16)⁺] |

TABLE 7

| Ex. | R¹ | R²/R³ | R⁴/R⁵ | R⁶/R⁷/R⁸/R⁹ | R¹⁰/R¹¹ | DATA |
|---|---|---|---|---|---|---|
| 9 | Ph | Me/Me | H/OH | H/H/H/H | H/H | [free base] FAB-MS(m/z); 254 [(M + 1)⁺] |
| 10 | Ph | Me/Me | H/H | H/H/H/H | Me/H | [HCl salt] FAB-MS(m/z); 252 (M + 1)⁺ ¹H NMR(DMSO-d6): 0.42(3H, s), 1.35(3H, s), 2.28(3H, t, J = 5.07 Hz), 2.80(1H, d, J = 16.6 Hz), 3.55(1H, d, J = 16.6 Hz), 7.35-7.55(9H, m), 9.31-9.61(2H, br). |
| 11 | Ph | Me/Me | H/H | H/H/H/H | Me/Me | [HCl salt] FAB-MS(m/z); 266 [(M + 1)⁺] |
| 12 | 2-Me-Ph | Me/Me | H/H | H/H/H/H | H/H | [HCl salt] FAB-MS(m/z); 252 [(M + 1)⁺] |
| 13 | 3-Me-Ph | Me/Me | H/H | H/H/H/H | H/H | [fumarate] FAB-MS(m/z); 252 [(M + 1)⁺] |
| 14 | 4-Me-Ph | Me/Me | H/H | H/H/H/H | H/H | [HCl salt] FAB-MS(m/z); 252 [(M + 1)⁺] |
| 15 | 2-F-Ph | Me/Me | H/H | H/H/H/H | H/H | [HCl salt] FAB-MS(m/z); 256 [(M + 1)⁺] |
| 16 | 3-F-Ph | Me/Me | H/H | H/H/H/H | H/H | [fumarate] FAB-MS(m/z); 256 [(M + 1)⁺] |
| 17 | 4-F-Ph | Me/Me | H/H | H/H/H/H | H/H | [fumarate] FAB-MS(m/z); 256 (M + 1)⁺ ¹H NMR(CD₃OD): 0.76(3H, s), |

TABLE 7-continued

| Ex. | R¹ | R²<br>R³ | R⁴<br>R⁵ | R⁶/R⁷<br>R⁸/R⁹ | R¹⁰<br>R¹¹ | DATA |
|---|---|---|---|---|---|---|
| | | | | | | 1.27(3H, s), 2.88(1H, d, J = 16.6 Hz), 2.99(1H, d, J = 16.6 Hz), 6.68(2H, s), 7.12-7.21(4H, m), 7.30-7.50(4H, m). |

TABLE 8

| Ex. | R¹ | R²<br>R³ | R⁴<br>R⁵ | R⁶/R⁷<br>R⁸/R⁹ | R¹⁰<br>R¹¹ | DATA |
|---|---|---|---|---|---|---|
| 18 | 2-OMe-Ph | Me<br>Me | H<br>H | H/H<br>H/H | H<br>H | [HCl salt] FAB-MS(m/z); 268 [(M + 1)⁺]<br>¹H NMR (CD₃OD): 0.92(3H, s), 1.34(3H, s), 2.82(1H, d, J = 15.9 Hz), 2.87(1H, d, J = 15.9 Hz), 4.00(3H, s), 6.34(1H, d, J = 8.05 Hz), 6.83(1H, t, J = 7.63 Hz), 7.19(1H, d, J = 7.93 z), 7.31-7.50(5H, m). |
| 19 | 3-OMe-Ph | Me<br>Me | H<br>H | H/H<br>H/H | H<br>H | [free base] FAB-MS(m/z); 268 [(M + 1)⁺] |
| 20 | 4-OMe-Ph | Me<br>Me | H<br>H | H/H<br>H/H | H<br>H | [HCl salt] FAB-MS(m/z); 268 [(M + 1)⁺] |
| 21 | 3-OH-Ph | Me<br>Me | H<br>H | H/H<br>H/H | H<br>H | [free base] FAB-MS(m/z); 254 [(M + 1)⁺]<br>¹H NMR(DMSO-d₆): 0.58(3H, s), 1.01(3H, s), 2.62(1H, d, J = 15.1 Hz), 2.70(1H, d, J = 15.1 Hz), 6.49-6.65(3H, m), 7.01(1H, t, J = 7.88), 7.15-7.27(4H, m), 9.08(1H, s). |
| 22 | 2-thienyl | Me<br>Me | H<br>H | H/H<br>H/H | H<br>H | [fumarate] FAB-MS(m/z); 243 [M⁺] |
| 23 | Me | Me<br>Me | H<br>H | H/H<br>H/H | H<br>H | [HCl salt] FAB-MS(m/z); 176 (M + 1)⁺]<br>¹H NMR(DMSO-d₆): 1.04(3H, s), 1.09(3H, s), 1.45(3H, s), 2.74(1H, d, J = 15.9 Hz), 2.97(1H, d, J = 15.9 Hz), 7.23-7.35(3H, m), 7.48-7.55(1H, m), 8.27-8.46(3H, br). |
| 24 | Me | Me<br>Me | Me<br>H | H/H<br>H/H | H<br>H | [HCl salt] EI-MS(m/z); 189 [M⁺] |
| 25 | Me | Me<br>Me | H<br>Me | H/H<br>H/H | H<br>H | [HCl salt] EI-MS(m/z); 189 [M⁺] |
| 26 | Me | Me<br>Me | Me<br>Me | H/H<br>H/H | H<br>H | [HCl salt] FAB-MS(m/z); 204 [(M + 1)⁺] |

TABLE 9

| Ex. | R¹ | R²<br>R³ | R⁴<br>R⁵ | R⁶/R⁷<br>R⁸/R⁹ | R¹⁰<br>R¹¹ | DATA |
|---|---|---|---|---|---|---|
| 27 | Me | Me<br>Me | OMe<br>H | H/H<br>H/H | H<br>H | [HCl salt] FAB-MS(m/z); 206 [(M + 1)⁺] |
| 28 | Me | Me<br>Me | H<br>H | Me/H<br>H/H | H<br>H | [HCl salt] EI-MS(m/z); 189 [M⁺] |
| 29 | Me | Me<br>Me | H<br>H | F/H<br>H/H | H<br>H | [HCl salt] FAB-MS(m/z); 194 (M + 1)⁺]<br>¹H NMR(DMSO-d₆): 1.07(3H, s), 1.11(3H, s), 1.46(3H, s), 2.78(1H, d, J = 16.0 Hz), 2.99(1H, d, J = 16.0 Hz), 7.13-7.19(1H, m), 7.33-7.43(2H, m), 8.56(3H, brs). |
| 30 | Me | Me<br>Me | H<br>H | CF₃/H<br>H/H | H<br>H | [HCl salt] FAB-MS(m/z); 244 [(M + 1)⁺] |
| 31 | Me | Me<br>Me | H<br>H | H/Me<br>H/H | H<br>H | [HCl salt] EI-MS(m/z); 189 [M⁺]<br>¹H NMR(DMSO-d₆): 1.02(3H, s), 1.09(3H, s), 1.43(3H, s), 2.30(3H, s), 2.67(1H, d, J = 15.9 Hz), 2.95(1H, d, J = 15.9 Hz), 7.05-7.10(2H, m), 7.40(1H, d, J = 7.7 Hz), 8.38(3H, brs). |
| 32 | Me | Me<br>Me | H<br>H | H/OMe<br>H/H | H<br>H | [HCl salt] FAB-MS(m/z); 206 [(M + 1)⁺]<br>¹H NMR(DMSO-d₆): 1.00(3H, s), 1.09(3H, s), 1.41(3H, s), 2.66(1H, d, J = 15.9 Hz), 2.98(1H, d, J = 15.9 Hz), |

TABLE 9-continued

| Ex. | R¹ | R² R³ | R⁴ R⁵ | R⁶/R⁷ R⁸/R⁹ | R¹⁰ R¹¹ | DATA |
|---|---|---|---|---|---|---|
|  |  |  |  |  |  | 3.75(3H, s), 6.80-6.86(2H, m), 7.38-7.42(1H, m), 8.20(3H, br). |
| 33 | Me | Me Me | H H | H/F H/H | H H | [HCl salt] FAB-MS(m/z); 194 [(M + 1)⁺] $^1$H NMR(DMSO-d$_6$): 1.02(3H, s), 1.08(3H, s), 1.43(3H, s), 2.73(1H, d, J = 16.2 Hz), 2.99(1H, d, J = 16.2 Hz), 7.07-7.15(2H, m), 7.55(1H, dd, J = 9.2, 5.4 Hz), 8.33(3H, br). |
| 34 | Me | Me Me | H H | H/Cl H/H | H H | [HCl salt] FAB-MS(m/z); 193 [(M − 16)⁺] |

TABLE 10

| Ex. | R¹ | R² R³ | R⁴ R⁵ | R⁶/R⁷ R⁸/R⁹ | R¹⁰ R¹¹ | DATA |
|---|---|---|---|---|---|---|
| 35 | Me | Me Me | H H | H/CF$_3$ H/H | H H | [HCl salt] FAB-MS(m/z); 244 [(M + 1)⁺] |
| 36 | Me | Me Me | H H | H/H Me/H | H H | [HCl salt] EI-MS(m/z); 189 [M⁺] $^1$H NMR(DMSO-d$_6$): 1.03(3H, s), 1.08(3H, s), 1.43(3H, s), 2.31(3H, s), 2.67(1H, d, J = 15.6 Hz), 2.92(1H, d, J = 15.6 Hz), 7.11(1H, brd, J = 7.7 Hz), 7.15(1H, d, J = 7.7 Hz), 7.34(1H, brs), 8.41(3H, brs). |
| 37 | Me | Me Me | H H | H/H OH/H | H H | [HCl salt] EI-MS(m/z); 189 [M⁺] $^1$H NMR(DMSO-d$_6$): 1.02(3H, s), 1.08(3H, s), 1.39(3H, s), 2.60(1H, d, J = 15.3 Hz), 2.83(1H, d, J = 15.3 Hz), 6.72(1H, dd, J = 8.1, 2.1 Hz), 6.87(1H, d, J = 2.1 Hz), 7.04(1H, d, J = 8.1 Hz), 8.24(3H, brs), 9.47(1H, s). |
| 38 | Me | Me Me | H H | H/H OMe/H | H H | [HCl salt] FAB-MS(m/z); 206 [(M + 1)⁺] $^1$H NMR(DMSO-d$_6$): 1.04(3H, s), 1.07(3H, s), 1.43(3H, s), 2.66(1H, d, J = 15.6 Hz), 2.86(1H, d, J = 15.6 Hz), 3.76(3H, s), 6.87(1H, dd, J = 2.5, 8.2 Hz), 7.14-7.18(2H, m), 8.37(3H, brs). |
| 39 | Me | Me Me | H H | H/H OEt/H | H H | [HCl salt] EI-MS(m/z); 219 [M⁺] |
| 40 | Me | Me Me | H H | H/H OiPr/H | H H | [HCl salt] EI-MS(m/z); 233 [M⁺] $^1$H NMR(DMSO-d$_6$): 1.04(3H, s), 1.07(3H, s), 1.27(3H, d, J = 6.0 Hz), 1.28(3H, d, J = 6.0 Hz), 1.42(3H, s), 2.65(1H, d, J = 15.5 Hz), 2.84(1H, d, J = 15.5 Hz), 4.59(1H, m), 6.83(1H, dd, J = 8.3, 2.3 Hz), 7.10(1H, d, J = 2.3 Hz), 7.14(1H, d, J = 8.3 Hz), 8.37(3H, brs). |
| 41 | Me | Me Me | H H | H/H F/H | H H | [HCl salt] FAB-MS(m/z); 194 (M + 1)⁺] $^1$H NMR(DMSO-d$_6$): 1.06(3H, s), 1.07(3H, s), 1.45(3H, s), 2.72(1H, d, J = 15.6 Hz), 2.97(1H, d, J = 15.6 Hz), 7.09-7.16(1H, m), 7.29(1H, dd, J = 8.3, 5.2 Hz), 7.44(1H, dd, J = 9.2, 2.6 Hz), 8.62(3H, brs). |

TABLE 11

| Ex. | R¹ | R² R³ | R⁴ R⁵ | R⁶/R⁷ R⁸/R⁹ | R¹⁰ R¹¹ | DATA |
|---|---|---|---|---|---|---|
| 42 | Me | Me Me | H H | H/H Br/H | H H | [HCl salt] EI-MS(m/z); 253, 255 [M⁺] $^1$H NMR(DMSO-d$_6$): 1.05(3H, s), 1.06(3H, s), 1.44(3H, s), 2.72(1H, d, J = 16.1 Hz), 2.91(1H, d, J = 16.1 Hz), 7.25(1H, d, J = 8.1 Hz), 7.50(1H, dd, |

TABLE 11-continued

| Ex. | R¹ | R²/R³ | R⁴/R⁵ | R⁶/R⁷ R⁸/R⁹ | R¹⁰/R¹¹ | DATA |
|---|---|---|---|---|---|---|
| | | | | | | J = 8.1, 1.8 Hz), 7.74(1H, d, J = 1.8 Hz), 8.53(3H, brs). |
| 43 | Me | Me Me | H H | H/H CF₃/H | H H | [HCl salt] FAB-MS(m/z); 244 [(M + 1)⁺] ¹H NMR(DMSO-d₆): 1.06(3H, s), 1.08(3H, s), 1.46(3H, s), 2.84(1H, d, J = 16.3 Hz), 3.02(16.3 Hz), 3.19-3.50(1H, br), 7.50(1H, d, J = 7.8 Hz), 7.66(1H, brd, J = 7.8 Hz), 7.94(1H, brs), 8.20-8.56(2H, br). |
| 44 | Me | Me Me | H H | H/H CN/H | H H | [HCl salt] EI-MS(m/z); 200 [M⁺] ¹H NMR(DMSO-d₆): 1.04(3H, s), 1.08(3H, s), 1.49(3H, s), 2.85(1H, d, J = 16.7 Hz), 3.07(1H, d, J = 16.7 Hz), 7.51(1H, d, J = 7.9 Hz), 7.80(1H, dd, J = 7.9, 1.5 Hz), 8.00(1H, brs), 8.62(3H, br). |
| 45 | Me | Me Me | H H | H/H vinyl/H | H H | [HCl salt] EI-MS(m/z); 201 [M⁺] |
| 46 | Me | Me Me | H H | H/H 1-Pip/H | H H | [2HCl salt] FAB-MS(m/z); 259 [(M + 1)⁺] |
| 47 | Me | Me Me | H H | H/H H/Me | H H | [HCl salt] EI-MS(m/z); 189 [M⁺] |
| 48 | Me | Me Me | H H | H/H H/F | H H | [HCl salt] EI-MS(m/z); 193 [M⁺] ¹H NMR(DMSO-d₆): 1.06(3H, s), 1.10(3H, s), 1.51(3H, s), 2.79(1H, d, J = 16.2 Hz), 3.03(1H, d, J = 16.2 Hz), 7.05-7.15(2H, m),, 7.38(1H, dt, J = 5.1, 7.8 Hz), 8.42(3H, br). |
| 49 | Me | Me Me | H H | H/H H/CF₃ | H H | [HCl salt] FAB-MS(m/z); 244 [(M + 1)⁺] |

TABLE 12

| Ex. | R¹ | R²/R³ | R⁴/R⁵ | R⁶/R⁷ R⁸/R⁹ | R¹⁰/R¹¹ | DATA |
|---|---|---|---|---|---|---|
| 50 | Me | Me Me | H H | F/H H/Br | H H | [HCl salt] ESI-MS(m/z); 273 [(M + 1)⁺] |
| 51 | Me | Me Me | H H | F/H H/Et | H H | [HCl salt] EI-MS(m/z); 221 [M⁺] |
| 52 | Me | Me Me | H H | F/H H/vinyl | H H | [HCl salt] EI-MS(m/z); 219 [M⁺] |
| 53 | Me | Me Me | H H | Br/H H/F | H H | [HCl salt] EI-MS(m/z); 271, 273 [M⁺] |
| 54 | Me | Me Me | H H | H/OMe OMe/H | H H | [HCl salt] FAB-MS(m/z); 219 [(M − 16)⁺] |
| 55 | Me | Me Me | H H | H/OMe H/Br | H H | [HCl salt] FAB-MS(m/z); 267, 269 [(M − 16)⁺] |
| 56 | Me | Me Me | H H | H/H F/OMe | H H | [HCl salt] FAB-MS(m/z); 224 [(M + 1)⁺] |
| 57 | CF₃ | Me Me | H H | H/H H/H | H H | [HCl salt] FAB-MS(m/z); 230 [(M + 1)⁺] |
| 58 | Et | Me Me | H H | H/H H/H | H H | [HCl salt] FAB-MS(m/z); 173 [(M − 16)⁺] ¹H NMR(CD3OD): 1.02(3H, t, J = 7.5 Hz), 1.16(3H, s), 1.23(3H, s), 1.84-1.97(1H, m), 1.99-2.10(1H, m), 2.89(2H, t, 16.7 Hz), 7.25-7.41(4H, m). |
| 59 | Et | Me Me | H H | Me/H H/H | H H | [HCl salt] EI-MS(m/z); 203 [M⁺] |

TABLE 13

| Ex. | R¹ | R²/R³ | R⁴/R⁵ | R⁶/R⁷ R⁸/R⁹ | R¹⁰/R¹¹ | DATA |
|---|---|---|---|---|---|---|
| 60 | i-Pr | Me Me | H H | H/H H/H | H H | [HCl salt] FAB-MS(m/z); 204 [(M + 1)⁺] ¹H NMR(CD₃OD): 0.90(3H, d, J = 6.8 Hz), 1.10(3H, d, J = 6.8 Hz), 1.10(3H, s), 1.39(1H, s), 2.29-2.40(1H, m), |

TABLE 13-continued

| Ex. | R¹ | R²/R³ | R⁴/R⁵ | R⁶/R⁷ R⁸/R⁹ | R¹⁰/R¹¹ | DATA |
|---|---|---|---|---|---|---|
| | | | | | | 2.71(1H, d, J = 16.1 Hz), 3.05(1H, d, J = 16.1 Hz), 7.23-7.40(4H, m). |
| 61 | n-Bu | Me/Me | H/H | H/H | H/H | [HCl salt] FAB-MS(m/z); 218 [(M + 1)⁺] |
| 62 | c-Hex | Me/Me | H/H | H/H | H/H | [fumarate] FAB-MS(m/z); 244 [(M + 1)⁺] |
| 63 | Bn | Me/Me | H/H | H/H | H/H | [fumarate] FAB-MS(m/z); 252 [(M + 1)⁺] |
| 64 | Me | Me/Et | H/H | H/H Me/H | H/H | [HCl salt] EI-MS(m/z); 203 [M⁺] |
| 65 | Me | Et/Me | H/H | H/H Me/H | H/H | [HCl salt] EI-MS(m/z); 203 [M⁺] |
| 66 | Me | Me/c-Pr | H/H | H/H H/H | H/H | [HCl salt] FAB-MS(m/z); 157 [(M − 16)⁺]<br>¹H NMR (DMSO-d₆): 0.56-0.63(1H, m), 0.69-0.76(1H, m), 0.87-0.95(1H, m), 1.09-1.16(1H, m), 1.39(3H, s), 2.77(1H, d, J = 16.5 Hz), 3.31(1H, d, J = 16.5 Hz), 7.25-7.40(3H, m), 7.56-7.61(1H, m), 8.37(3H, brs). |
| 67 | Me | Me/c-Pn | H/H | H/H H/H | H/H | [HCl salt] EI-MS(m/z); 201 [M⁺] |

TABLE 14

| Ex. | STRUCTURE | DATA |
|---|---|---|
| 68 | (2,4-dimethyl-4,6-dimethyl-5,6-dihydro-4H-cyclopenta[b]thiophen-4-amine structure) | [HCl salt] FAB-MS(m/z); 179 [(M − 15)⁺] ¹H NMR(DMSO-d₆): 1.07(3H, s), 1.18(3H, s), 1.40(3H, s), 2.42(3H, s), 2.64(1H, d, J = 15 Hz), 2.96(1H, d, J = 15 Hz), 6.76(1H, s), 8.35(3H, br). |
| 69 | (3-phenyl-2,2-dimethyl-2,3-dihydrobenzofuran-3-amine structure) | [HCl salt] FAB-MS(m/z); 239 [M⁺] ¹H NMR(DMSO-d₆): 0.85 (3H, s), 1.66(3H, s), 6.95-7.13(2H, m), 7.33-7.54(7H, m), 9.37(3H, br). |

TABLE 15

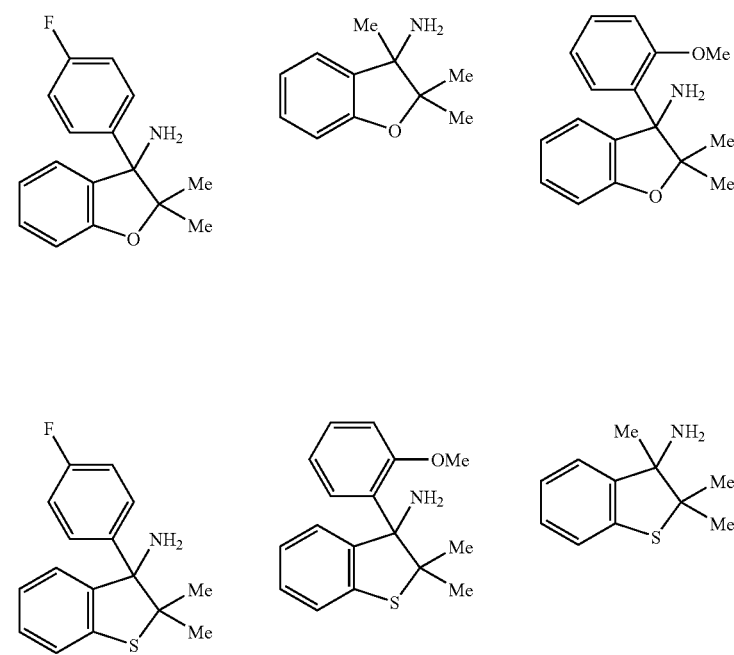

TABLE 15-continued
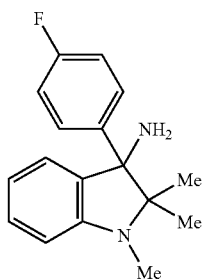 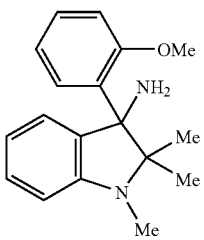 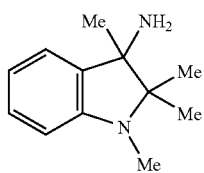
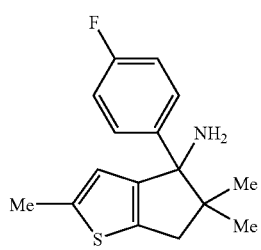 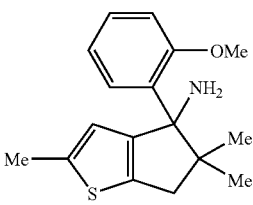 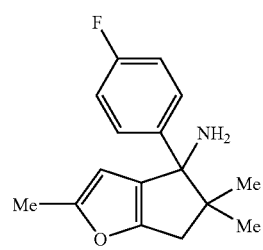
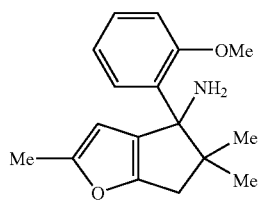 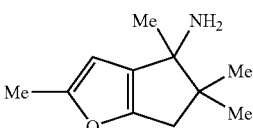 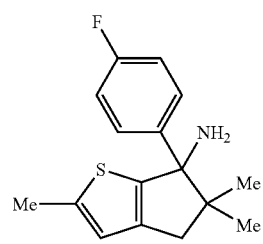
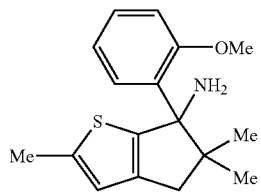 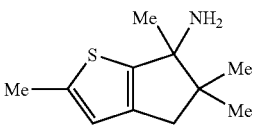 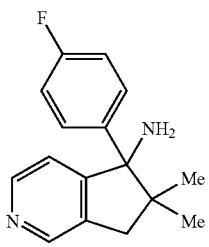
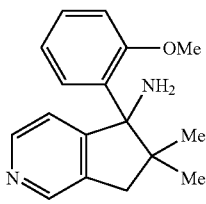 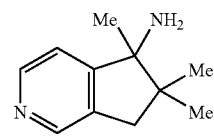 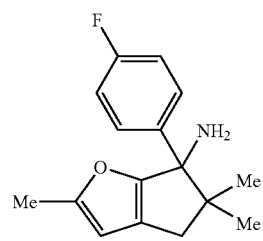

The invention claimed is:

1. A compound represented by the following formula (Ia) or a pharmaceutically acceptable salt thereof:

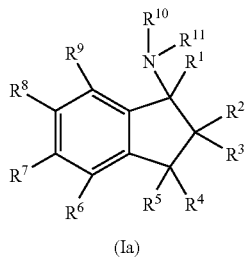

[Chem. 9]

(Ia)

wherein $R^1$ is lower alkyl, cycloalkyl, lower alkylene-aryl, aryl which may be substituted, heteroaryl which may be substituted, or lower alkyl substituted with one or more halogens;
$R^2$ and $R^3$ independently represent lower alkyl, or aryl;
$R^4$ and $R^5$ independently represent a hydrogen atom, lower alkyl, —O-lower alkyl, —OH, lower alkylene-OH, or lower alkylene-O-lower alkyl;
$R^6$ to $R^9$ independently represent a hydrogen atom, lower alkyl, —O-lower alkyl, a halogen atom, lower alkyl substituted with one or more halogens, OH, CN, lower alkenyl, or a nitrogen-containing heterocyclic group; and
$R^{10}$ and $R^{11}$ independently represent a hydrogen atom, or lower alkyl,
provided that $R^2$ and $R^3$ may be taken together with the adjacent carbon atom to form cycloalkyl.

2. A compound or a pharmaceutically acceptable salt thereof according to claim 1, wherein $R^4$, $R^5$, $R^{10}$, and $R^{11}$ are each a hydrogen atom.

3. A compound or a pharmaceutically acceptable salt thereof according to claim 2, wherein $R^2$ and $R^3$ independently represent lower alkyl, or are cycloalkyl formed in combination with the adjacent carbon atom.

4. A compound or a pharmaceutically acceptable salt thereof according to claim 1, which is selected from the group consisting of 2,2-dimethyl-1-phenylindan-1-amine, 1-(4-fluorophenyl)-2,2-dimethylindan-1-amine, 1-(2-methoxyphenyl)-2,2-dimethylindan-1-amine, 1-(3-methoxyphenyl)-2,2-dimethylindan-1-amine, 1,2,2-trimethylindan-1-amine, 1,2,2,5-tetramethylindan-1-amine, 1,2,2,6-tetramethylindan-1-amine, 4-fluoro-1,2,2-trimethylindan-1-amine, 5-fluoro-1,2,2-trimethylindan-1-amine, 7-fluoro-1,2,2-trimethylindan-1-amine, 5-methoxy-1,2,2-trimethylindan-1-amine, 6-methoxy-1,2,2-trimethylindan-1-amine, 6-isopropoxy-1,2,2-trimethylindan-1-amine, 1-ethyl-2,2-dimethylindan-1-amine, 1-isopropyl-2,2-dimethylindan-1-amine, 1'-methyl-1',3-dihydrospiro[cyclopropan-1,2'-inden]-1'-amine, and a pharmaceutically acceptable salt thereof.

5. A compound or a pharmaceutically acceptable salt thereof according to claim 1, which is 1,2,2,6-tetramethylindan-1-amine or a pharmaceutically acceptable salt thereof.

6. A compound or a pharmaceutically acceptable salt thereof according to claim 1, which is 1,2,2-trimethylindan-1-amine or a pharmaceutically acceptable salt thereof.

7. A compound or a pharmaceutically acceptable salt thereof according to claim 1, which is 6-methoxy-1,2,2-trimethylindan-1-amine or a pharmaceutically acceptable salt thereof.

8. A pharmaceutical composition comprising a compound or a pharmaceutically acceptable salt thereof according to any one of claims 1, 5, 6 and 7, together with a pharmaceutically acceptable carrier.

9. A method of antagonizing NMDA receptor, comprising the steps of administering a compound or a pharmaceutically acceptable salt thereof according to any one of claims 1, 5, 6 and 7 to a patient in need thereof.

10. A method for treating dementia, comprising administering a therapeutically effective amount of a compound or a pharmaceutically acceptable salt thereof according to any one of claims 1, 5, 6 and 7 to a patient in need thereof.

11. A compound or a pharmaceutically acceptable salt thereof according to any one of claims 1, 5, 6 and 7 as a single optical isomer.

12. A pharmaceutical composition, comprising a compound or a pharmaceutically acceptable salt thereof according to claim 11, together with a pharmaceutically acceptable carrier.

13. A method of antagonizing NMDA receptor, comprising the steps of administering a compound or a pharmaceutically acceptable salt thereof according to claim 11 to a patient in need thereof.

14. A method for treating dementia, comprising administering a therapeutically effective amount of a compound or a pharmaceutically acceptable salt thereof according to claim 11 to a patient in need thereof.

* * * * *